(12) United States Patent
Adamek-Bowers et al.

(10) Patent No.: US 12,702,544 B2
(45) **Date of Patent: *Aug. 11, 2026**

(54) EMBEDDED RADIOPAQUE MARKER IN ADAPTIVE SEAL

(71) Applicant: BOSTON SCIENTIFIC SCIMED, INC., Maple Grove, MN (US)

(72) Inventors: Jasper Ellington Adamek-Bowers, San Francisco, CA (US); Takashi H. Ino, San Jose, CA (US); Ali Salahieh, Saratoga, CA (US); Leticia Marquez Zuniga, Gilroy, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1045 days.

This patent is subject to a terminal disclaimer.

(21) Appl. No.: 17/879,292

(22) Filed: Aug. 2, 2022

(65) Prior Publication Data

US 2022/0370685 A1 Nov. 24, 2022

Related U.S. Application Data

(63) Continuation of application No. 16/285,337, filed on Feb. 26, 2019, now Pat. No. 11,439,732.

(Continued)

(51) Int. Cl.
*A61F 2/24* (2006.01)

(52) U.S. Cl.
CPC .......... *A61F 2/2412* (2013.01); *A61F 2/2409* (2013.01); *A61F 2/2418* (2013.01);

(Continued)

(58) Field of Classification Search
CPC .... A61F 2/2409; A61F 2/2412; A61F 2/2418; A61F 2/2427; A61F 2250/0098
See application file for complete search history.

(56) References Cited

U.S. PATENT DOCUMENTS 15,192 A 6/1856 Peale
2,682,057 A 6/1954 Lord (Continued)

FOREIGN PATENT DOCUMENTS

AU 2002329324 B2 7/2007
AU 2011202667 B2 9/2012

(Continued)

OTHER PUBLICATIONS

US 8,062,356 B2, 11/2011, Salahieh et al. (withdrawn)

(Continued)

*Primary Examiner* — Bruce E Snow
(74) *Attorney, Agent, or Firm* — Seager, Tufte & Wickhem LLP

(57) ABSTRACT

A seal member for use with a replacement heart valve implant may include a tubular polymeric seal element configured to be disposed on an outer surface of a replacement heart valve implant, the tubular polymeric seal element defining a central longitudinal axis; and a reinforcement strip fixedly attached to the tubular polymeric seal element proximate a first end of the tubular polymeric seal element, the reinforcement strip extending circumferentially around the central longitudinal axis. The reinforcement strip may include a radiopaque element extending circumferentially around the central longitudinal axis.

20 Claims, 6 Drawing Sheets

Related U.S. Application Data

(60) Provisional application No. 62/635,236, filed on Feb. 26, 2018.

(52) U.S. Cl.
CPC .......... *A61F 2/2427* (2013.01); *A61F 2/2415* (2013.01); *A61F 2250/0098* (2013.01)

(56) References Cited

U.S. PATENT DOCUMENTS

| | | | |
|---|---|---|---|
| 2,701,559 | A | 2/1955 | Cooper |
| 2,832,078 | A | 4/1958 | Williams |
| 3,029,819 | A | 4/1962 | Starks |
| 3,099,016 | A | 7/1963 | Lowell |
| 3,113,586 | A | 12/1963 | Edmark |
| 3,130,418 | A | 4/1964 | Head et al. |
| 3,143,742 | A | 8/1964 | Cromie |
| 3,221,006 | A | 11/1965 | Moore et al. |
| 3,334,629 | A | 8/1967 | Cohn |
| 3,365,728 | A | 1/1968 | Edwards et al. |
| 3,367,364 | A | 2/1968 | Cruz et al. |
| 3,409,013 | A | 11/1968 | Henry |
| 3,445,916 | A | 5/1969 | Schulte |
| 3,503,079 | A | 3/1970 | Smith |
| 3,540,431 | A | 11/1970 | Mobin-Uddin |
| 3,546,711 | A | 12/1970 | Boyros |
| 3,548,417 | A | 12/1970 | Kischer et al. |
| 3,551,913 | A | 1/1971 | Shiley et al. |
| 3,570,014 | A | 3/1971 | Hancock |
| 3,587,115 | A | 6/1971 | Shiley |
| 3,592,184 | A | 7/1971 | Watkins et al. |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Goodenough et al. |
| 3,725,961 | A | 4/1973 | Magovern et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 3,983,581 | A | 10/1976 | Angell et al. |
| 3,997,923 | A | 12/1976 | Possis |
| 4,035,849 | A | 7/1977 | Angell et al. |
| 4,056,854 | A | 11/1977 | Boretos et al. |
| 4,084,268 | A | 4/1978 | Ionescu et al. |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos et al. |
| 4,291,420 | A | 9/1981 | Reul |
| 4,297,749 | A | 11/1981 | Davis et al. |
| 4,323,358 | A | 4/1982 | Lentz et al. |
| 4,326,306 | A | 4/1982 | Poler |
| 4,339,831 | A | 7/1982 | Johnson |
| 4,340,977 | A | 7/1982 | Brownlee et al. |
| 4,343,048 | A | 8/1982 | Ross et al. |
| 4,345,340 | A | 8/1982 | Rosen |
| 4,373,216 | A | 2/1983 | Klawitter |
| 4,388,735 | A | 6/1983 | Ionescu et al. |
| 4,406,022 | A | 9/1983 | Roy |
| 4,423,809 | A | 1/1984 | Mazzocco |
| 4,425,908 | A | 1/1984 | Simon |
| 4,470,157 | A | 9/1984 | Love |
| 4,473,423 | A | 9/1984 | Kolff |
| 4,484,365 | A | 11/1984 | Murguet et al. |
| 4,484,579 | A | 11/1984 | Meno et al. |
| 4,490,859 | A | 1/1985 | Black et al. |
| 4,501,030 | A | 2/1985 | Lane |
| 4,510,628 | A | 4/1985 | Kolff |
| 4,531,943 | A | 7/1985 | Tassel et al. |
| 4,535,483 | A | 8/1985 | Klawitter et al. |
| 4,574,803 | A | 3/1986 | Storz |
| 4,580,568 | A | 4/1986 | Gianturco |
| 4,592,340 | A | 6/1986 | Boyles |
| 4,602,911 | A | 7/1986 | Ahmadi et al. |
| 4,605,407 | A | 8/1986 | Black et al. |
| 4,610,688 | A | 9/1986 | Silvestrini et al. |
| 4,612,011 | A | 9/1986 | Kautzky |
| 4,617,932 | A | 10/1986 | Kornberg |
| 4,643,732 | A | 2/1987 | Pietsch et al. |
| 4,647,283 | A | 3/1987 | Carpentier et al. |
| 4,648,881 | A | 3/1987 | Carpentier et al. |
| 4,655,218 | A | 4/1987 | Kulik et al. |
| 4,655,771 | A | 4/1987 | Wallsten et al. |
| 4,662,885 | A | 5/1987 | DiPisa |
| 4,665,906 | A | 5/1987 | Jervis |
| 4,680,031 | A | 7/1987 | Alonso |
| 4,692,164 | A | 9/1987 | Dzemeshkevich et al. |
| 4,705,516 | A | 11/1987 | Barone et al. |
| 4,710,192 | A | 12/1987 | Liotta et al. |
| 4,733,665 | A | 3/1988 | Palmaz et al. |
| 4,739,759 | A | 4/1988 | Rexroth et al. |
| 4,755,181 | A | 7/1988 | Igoe |
| 4,759,758 | A | 7/1988 | Gabbay |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,819,751 | A | 4/1989 | Shimada et al. |
| 4,829,990 | A | 5/1989 | Thuroff et al. |
| 4,834,755 | A | 5/1989 | Silvestrini et al. |
| 4,851,001 | A | 7/1989 | Taheri |
| 4,856,516 | A | 8/1989 | Hillstead |
| 4,865,600 | A | 9/1989 | Carpentier et al. |
| 4,872,874 | A | 10/1989 | Taheri |
| 4,873,978 | A | 10/1989 | Ginsburg |
| 4,878,495 | A | 11/1989 | Grayzel |
| 4,878,906 | A | 11/1989 | Lindemann et al. |
| 4,883,458 | A | 11/1989 | Shiber |
| 4,885,005 | A | 12/1989 | Nashef et al. |
| 4,909,252 | A | 3/1990 | Goldberger |
| 4,917,102 | A | 4/1990 | Miller et al. |
| 4,922,905 | A | 5/1990 | Strecker |
| 4,927,426 | A | 5/1990 | Dretler |
| 4,954,126 | A | 9/1990 | Wallsten |
| 4,966,604 | A | 10/1990 | Reiss |
| 4,969,890 | A | 11/1990 | Sugita et al. |
| 4,979,939 | A | 12/1990 | Shiber |
| 4,986,830 | A | 1/1991 | Owens et al. |
| 4,994,077 | A | 2/1991 | Dobben |
| 5,002,556 | A | 3/1991 | Ishida et al. |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,047,050 | A | 9/1991 | Arpesani |
| 5,064,435 | A | 11/1991 | Porter |
| 5,080,668 | A | 1/1992 | Bolz et al. |
| 5,085,635 | A | 2/1992 | Cragg |
| 5,089,015 | A | 2/1992 | Ross |
| 5,122,154 | A | 6/1992 | Rhodes |
| 5,132,473 | A | 7/1992 | Furutaka et al. |
| 5,141,494 | A | 8/1992 | Danforth et al. |
| 5,152,771 | A | 10/1992 | Sabbaghian et al. |
| 5,159,937 | A | 11/1992 | Tremulis |
| 5,161,547 | A | 11/1992 | Tower |
| 5,163,953 | A | 11/1992 | Vince |
| 5,167,628 | A | 12/1992 | Boyles |
| 5,209,741 | A | 5/1993 | Spaeth |
| 5,215,541 | A | 6/1993 | Nashef et al. |
| 5,217,481 | A | 6/1993 | Barbara |
| 5,217,483 | A | 6/1993 | Tower |
| 5,238,004 | A | 8/1993 | Sahatjian et al. |
| 5,258,023 | A | 11/1993 | Reger |
| 5,258,042 | A | 11/1993 | Mehta |
| 5,282,847 | A | 2/1994 | Trescony et al. |
| 5,295,958 | A | 3/1994 | Shturman |
| 5,326,372 | A | 7/1994 | Mhatre et al. |
| 5,332,402 | A | 7/1994 | Teitelbaum |
| 5,336,258 | A | 8/1994 | Quintero et al. |

(56) References Cited

U.S. PATENT DOCUMENTS 5,350,398 A 9/1994 Pavcnik et al.
5,360,444 A 11/1994 Kusuhara
5,370,685 A 12/1994 Stevens
5,389,106 A 2/1995 Tower
5,397,351 A 3/1995 Pavcnik et al.
5,409,019 A 4/1995 Wilk
5,411,552 A 5/1995 Andersen et al.
5,425,739 A 6/1995 Jesser
5,425,762 A 6/1995 Muller
5,431,676 A 7/1995 Dubrul et al.
5,443,446 A 8/1995 Shturman
5,443,449 A 8/1995 Buelna
5,443,477 A 8/1995 Marin et al.
5,443,495 A 8/1995 Buscemi et al.
5,443,499 A 8/1995 Schmitt
5,469,868 A 11/1995 Reger
5,476,506 A 12/1995 Lunn
5,476,510 A 12/1995 Eberhardt et al.
5,480,423 A 1/1996 Ravenscroft et al.
5,480,424 A 1/1996 Cox
5,489,297 A 2/1996 Duran
5,500,014 A 3/1996 Quijano et al.
5,507,767 A 4/1996 Maeda et al.
5,522,881 A 6/1996 Lentz
5,534,007 A 7/1996 Germain et al.
5,545,133 A 8/1996 Burns et al.
5,545,209 A 8/1996 Roberts et al.
5,545,211 A 8/1996 An et al.
5,545,214 A 8/1996 Stevens
5,549,665 A 8/1996 Vesely et al.
5,554,185 A 9/1996 Block et al.
5,571,175 A 11/1996 Vanney et al.
5,571,215 A 11/1996 Sterman et al.
5,573,520 A 11/1996 Schwartz et al.
5,575,818 A 11/1996 Pinchuk
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,784 A 5/1997 Strecker
5,645,559 A 7/1997 Hachtman et al.
5,653,745 A 8/1997 Trescony et al.
5,662,671 A 9/1997 Barbut et al.
5,667,523 A 9/1997 Bynon et al.
5,674,277 A 10/1997 Freitag
5,681,345 A 10/1997 Euteneuer
5,693,083 A 12/1997 Baker et al.
5,693,088 A 12/1997 Lazarus
5,693,310 A 12/1997 Gries et al.
5,695,498 A 12/1997 Tower
5,709,713 A 1/1998 Evans et al.
5,713,951 A 2/1998 Garrison et al.
5,713,953 A 2/1998 Vallana et al.
5,716,370 A 2/1998 Williamson et al.
5,716,417 A 2/1998 Girard et al.
5,720,391 A 2/1998 Dohm et al.
5,725,549 A 3/1998 Lam
5,728,068 A 3/1998 Leone et al.
5,733,325 A 3/1998 Robinson et al.
5,735,842 A 4/1998 Krueger et al.
5,749,890 A 5/1998 Shaknovich
5,755,783 A 5/1998 Stobie et al.
5,756,476 A 5/1998 Epstein et al.
5,769,812 A 6/1998 Stevens et al.
5,769,882 A 6/1998 Fogarty et al.
5,772,609 A 6/1998 Nguyen et al.
5,776,188 A 7/1998 Shepherd et al.
5,782,904 A 7/1998 White et al.
5,800,456 A 9/1998 Maeda et al.
5,800,531 A 9/1998 Cosgrove et al.
5,807,405 A 9/1998 Vanney et al.
5,817,126 A 10/1998 Imran
5,824,037 A 10/1998 Fogarty et al.
5,824,041 A 10/1998 Lenker et al.
5,824,043 A 10/1998 Cottone
5,824,053 A 10/1998 Khosravi et al.
5,824,055 A 10/1998 Spiridigliozzi et al.
5,824,056 A 10/1998 Rosenberg
5,824,064 A 10/1998 Taheri
5,840,081 A 11/1998 Andersen et al.
5,843,158 A 12/1998 Lenker et al.
5,843,161 A 12/1998 Solovay
5,855,597 A 1/1999 Jayaraman
5,855,601 A 1/1999 Bessler et al.
5,855,602 A 1/1999 Angell
5,860,966 A 1/1999 Tower
5,860,996 A 1/1999 Urban et al.
5,861,024 A 1/1999 Rashidi
5,861,028 A 1/1999 Angell
5,868,783 A 2/1999 Tower
5,876,419 A 3/1999 Carpenter et al.
5,876,448 A 3/1999 Thompson et al.
5,885,228 A 3/1999 Rosenman et al.
5,888,201 A 3/1999 Stinson et al.
5,891,191 A 4/1999 Stinson
5,895,399 A 4/1999 Barbut et al.
5,906,619 A 5/1999 Olson et al.
5,907,893 A 6/1999 Zadno-Azizi et al.
5,910,154 A 6/1999 Tsugita et al.
5,911,734 A 6/1999 Tsugita et al.
5,925,063 A 7/1999 Khosravi
5,944,738 A 8/1999 Amplatz et al.
5,954,766 A 9/1999 Zadno-Azizi et al.
5,957,949 A 9/1999 Leonhardt et al.
5,968,070 A 10/1999 Bley et al.
5,984,957 A 11/1999 Laptewicz et al.
5,984,959 A 11/1999 Robertson et al.
5,993,469 A 11/1999 McKenzie et al.
5,997,557 A 12/1999 Barbut et al.
6,010,522 A 1/2000 Barbut et al.
6,015,431 A 1/2000 Thornton et al.
6,022,370 A 2/2000 Tower
6,027,520 A 2/2000 Tsugita et al.
6,027,525 A 2/2000 Suh et al.
6,042,598 A 3/2000 Tsugita et al.
6,042,607 A 3/2000 Williamson et al.
6,045,576 A 4/2000 Starr et al.
6,051,014 A 4/2000 Jang
6,059,827 A 5/2000 Fenton
6,074,418 A 6/2000 Buchanan et al.
6,093,203 A 7/2000 Uflacker
6,096,074 A 8/2000 Pedros
6,110,198 A 8/2000 Fogarty et al.
6,123,723 A 9/2000 Konya et al.
6,132,473 A 10/2000 Williams et al.
6,139,510 A 10/2000 Palermo
6,142,987 A 11/2000 Tsugita
6,146,366 A 11/2000 Schachar
6,162,245 A 12/2000 Jayaraman
6,165,200 A 12/2000 Tsugita et al.
6,165,209 A 12/2000 Patterson et al.
6,168,579 B1 1/2001 Tsugita
6,168,614 B1 1/2001 Andersen et al.
6,171,327 B1 1/2001 Daniel et al.
6,171,335 B1 1/2001 Wheatley et al.
6,179,859 B1 1/2001 Bates et al.
6,187,016 B1 2/2001 Hedges et al.
6,197,053 B1 3/2001 Cosgrove et al.
6,200,336 B1 3/2001 Pavcnik et al.
6,206,911 B1 3/2001 Milo
6,214,036 B1 4/2001 Letendre et al.
6,221,006 B1 4/2001 Dubrul et al.
6,221,091 B1 4/2001 Khosravi
6,221,096 B1 4/2001 Aiba et al.
6,221,100 B1 4/2001 Strecker
6,231,544 B1 5/2001 Tsugita et al.
6,231,551 B1 5/2001 Barbut
6,241,757 B1 6/2001 An et al.
6,245,102 B1 6/2001 Jayaraman
6,251,135 B1 6/2001 Stinson et al.
6,254,636 B1 7/2001 Peredo
6,258,114 B1 7/2001 Konya et al.
6,258,115 B1 7/2001 Dubrul
6,258,120 B1 7/2001 McKenzie et al.

(56) References Cited

U.S. PATENT DOCUMENTS 6,258,129 B1 7/2001 Dybdal et al.
6,267,783 B1 7/2001 Letendre et al.
6,270,513 B1 8/2001 Tsugita et al.
6,277,555 B1 8/2001 Duran et al.
6,299,637 B1 10/2001 Shaolian et al.
6,302,906 B1 10/2001 Goicoechea et al.
6,306,164 B1 10/2001 Kujawski
6,309,417 B1 10/2001 Spence et al.
6,312,465 B1 11/2001 Griffin et al.
6,319,281 B1 11/2001 Patel
6,327,772 B1 12/2001 Zadno-Azizi et al.
6,336,934 B1 1/2002 Gilson et al.
6,336,937 B1 1/2002 Vonesh et al.
6,338,735 B1 1/2002 Stevens
6,346,116 B1 2/2002 Brooks et al.
6,348,063 B1 2/2002 Yassour et al.
6,352,554 B2 3/2002 Paulis
6,352,708 B1 3/2002 Duran et al.
6,361,545 B1 3/2002 Macoviak et al.
6,363,938 B2 4/2002 Saadat et al.
6,364,895 B1 4/2002 Greenhalgh
6,371,970 B1 4/2002 Khosravi et al.
6,371,983 B1 4/2002 Lane
6,379,383 B1 4/2002 Palmaz et al.
6,387,122 B1 5/2002 Cragg
6,398,807 B1 6/2002 Chouinard et al.
6,402,736 B1 6/2002 Brown et al.
6,409,750 B1 6/2002 Hyodoh et al.
6,416,510 B1 7/2002 Altman et al.
6,425,916 B1 7/2002 Garrison et al.
6,440,164 B1 8/2002 DiMatteo et al.
6,454,799 B1 9/2002 Schreck
6,458,153 B1 10/2002 Bailey et al.
6,461,382 B1 10/2002 Cao
6,468,303 B1 10/2002 Amplatz et al.
6,468,660 B2 10/2002 Ogle et al.
6,475,239 B1 11/2002 Campbell et al.
6,482,228 B1 11/2002 Norred
6,485,501 B1 11/2002 Green
6,485,502 B2 11/2002 Michael et al.
6,488,704 B1 12/2002 Connelly et al.
6,494,909 B2 12/2002 Greenhalgh
6,503,272 B2 1/2003 Duerig et al.
6,508,803 B1 1/2003 Horikawa et al.
6,508,833 B2 1/2003 Pavcnik et al.
6,527,800 B1 3/2003 McGuckin et al.
6,530,949 B2 3/2003 Konya et al.
6,530,952 B2 3/2003 Vesely
6,537,297 B2 3/2003 Tsugita et al.
6,540,768 B1 4/2003 Diaz et al.
6,540,782 B1 4/2003 Snyders
6,558,417 B2 5/2003 Peredo
6,562,058 B2 5/2003 Seguin et al.
6,569,196 B1 5/2003 Vesely
6,572,643 B1 6/2003 Gharibadeh
6,585,766 B1 7/2003 Huynh et al.
6,592,546 B1 7/2003 Barbut et al.
6,592,614 B2 7/2003 Lenker et al.
6,605,112 B1 8/2003 Moll et al.
6,610,077 B1 8/2003 Hancock et al.
6,616,682 B2 9/2003 Joergensen et al.
6,622,604 B1 9/2003 Chouinard et al.
6,623,518 B2 9/2003 Thompson et al.
6,623,521 B2 9/2003 Steinke et al.
6,626,938 B1 9/2003 Butaric et al.
6,632,243 B1 10/2003 Zadno-Azizi et al.
6,635,068 B1 10/2003 Dubrul et al.
6,635,079 B2 10/2003 Unsworth et al.
6,635,080 B1 10/2003 Lauterjung et al.
6,652,571 B1 11/2003 White et al.
6,652,578 B2 11/2003 Bailey et al.
6,663,588 B2 12/2003 DuBois et al.
6,663,663 B2 12/2003 Kim et al.
6,663,667 B2 12/2003 Dehdashtian et al.
6,669,724 B2 12/2003 Park et al.
6,673,089 B1 1/2004 Yassour et al.
6,673,109 B2 1/2004 Cox
6,676,668 B2 1/2004 Mercereau et al.
6,676,692 B2 1/2004 Rabkin et al.
6,676,698 B2 1/2004 McGuckin et al.
6,682,543 B2 1/2004 Barbut et al.
6,682,558 B2 1/2004 Tu et al.
6,682,559 B2 1/2004 Myers et al.
6,685,739 B2 2/2004 DiMatteo et al.
6,689,144 B2 2/2004 Gerberding
6,689,164 B1 2/2004 Seguin
6,692,512 B2 2/2004 Jang
6,695,864 B2 2/2004 Macoviak et al.
6,695,865 B2 2/2004 Boyle et al.
6,702,851 B1 3/2004 Chinn et al.
6,712,842 B1 3/2004 Gifford et al.
6,712,843 B2 3/2004 Elliott
6,714,842 B1 3/2004 Ito
6,719,789 B2 4/2004 Cox
6,723,116 B2 4/2004 Taheri
6,729,356 B1 5/2004 Baker et al.
6,730,118 B2 5/2004 Spenser et al.
6,730,377 B2 5/2004 Wang
6,733,525 B2 5/2004 Yang et al.
6,736,846 B2 5/2004 Cox
6,752,828 B2 6/2004 Thornton
6,755,854 B2 6/2004 Gillick et al.
6,758,855 B2 7/2004 Fulton et al.
6,764,503 B1 7/2004 Ishimaru
6,764,509 B2 7/2004 Chinn et al.
6,767,345 B2 7/2004 Germain et al.
6,769,434 B2 8/2004 Liddicoat et al.
6,773,454 B2 8/2004 Wholey et al.
6,773,456 B1 8/2004 Gordon et al.
6,776,791 B1 8/2004 Stallings et al.
6,786,925 B1 9/2004 Schoon et al.
6,790,229 B1 9/2004 Berreklouw
6,790,230 B2 9/2004 Beyersdorf et al.
6,790,237 B2 9/2004 Stinson
6,792,979 B2 9/2004 Konya et al.
6,797,002 B2 9/2004 Spence et al.
6,814,746 B2 11/2004 Thompson et al.
6,814,754 B2 11/2004 Greenhalgh
6,821,297 B2 11/2004 Snyders
6,824,041 B2 11/2004 Grieder et al.
6,830,585 B1 12/2004 Artof et al.
6,837,901 B2 1/2005 Rabkin et al.
6,840,957 B2 1/2005 DiMatteo et al.
6,843,802 B1 1/2005 Villalobos et al.
6,849,085 B2 2/2005 Marton
6,863,668 B2 3/2005 Gillespie et al.
6,863,688 B2 3/2005 Ralph et al.
6,866,650 B2 3/2005 Stevens et al.
6,866,669 B2 3/2005 Buzzard et al.
6,872,223 B2 3/2005 Roberts et al.
6,872,226 B2 3/2005 Cali et al.
6,875,231 B2 4/2005 Anduiza et al.
6,881,220 B2 4/2005 Edwin et al.
6,883,522 B2 4/2005 Spence et al.
6,887,266 B2 5/2005 Williams et al.
6,890,340 B2 5/2005 Duane
6,893,459 B1 5/2005 Macoviak
6,893,460 B2 5/2005 Spenser et al.
6,896,690 B1 5/2005 Lambrecht et al.
6,905,743 B1 6/2005 Chen et al.
6,908,481 B2 6/2005 Cribier
6,911,036 B2 6/2005 Douk et al.
6,911,040 B2 6/2005 Johnson et al.
6,911,043 B2 6/2005 Myers et al.
6,936,058 B2 8/2005 Forde et al.
6,936,067 B2 8/2005 Buchanan
6,939,352 B2 9/2005 Buzzard et al.
6,951,571 B1 10/2005 Srivastava
6,951,573 B1 10/2005 Dilling
6,953,332 B1 10/2005 Kurk et al.
6,964,673 B2 11/2005 Tsugita et al.
6,969,395 B2 11/2005 Eskuri
6,972,025 B2 12/2005 WasDyke
6,974,464 B2 12/2005 Quijano et al.

(56) References Cited

U.S. PATENT DOCUMENTS 6,974,474 B2 12/2005 Pavcnik et al.
6,974,476 B2 12/2005 McGuckin et al.
6,979,350 B2 12/2005 Moll et al.
6,984,242 B2 1/2006 Campbell et al.
6,989,027 B2 1/2006 Allen et al.
7,004,176 B2 2/2006 Lau
7,011,681 B2 3/2006 Vesely
7,018,406 B2 3/2006 Seguin et al.
7,025,791 B2 4/2006 Levine et al.
7,037,331 B2 5/2006 Mitelberg et al.
7,041,132 B2 5/2006 Quijano et al.
7,044,966 B2 5/2006 Svanidze et al.
7,097,658 B2 8/2006 Oktay
7,108,715 B2 9/2006 Lawrence-Brown et al.
7,122,020 B2 10/2006 Mogul
7,125,418 B2 10/2006 Duran et al.
7,141,063 B2 11/2006 White et al.
7,147,663 B1 12/2006 Berg et al.
7,166,097 B2 1/2007 Barbut
7,172,625 B2 2/2007 Shu et al.
7,175,652 B2 2/2007 Cook et al.
7,175,653 B2 2/2007 Gaber
7,175,654 B2 2/2007 Bonsignore et al.
7,175,656 B2 2/2007 Khairkhahan
7,175,659 B2 2/2007 Hill et al.
7,189,258 B2 3/2007 Johnson et al.
7,191,018 B2 3/2007 Gielen et al.
7,201,772 B2 4/2007 Schwammenthal et al.
7,235,093 B2 6/2007 Gregorich
7,252,682 B2 8/2007 Seguin
7,258,696 B2 8/2007 Rabkin et al.
7,261,732 B2 8/2007 Justino
7,264,632 B2 9/2007 Wright et al.
7,267,686 B2 9/2007 DiMatteo et al.
7,276,078 B2 10/2007 Spenser et al.
7,318,278 B2 1/2008 Zhang et al.
7,322,932 B2 1/2008 Xie et al.
7,326,236 B2 2/2008 Andreas et al.
7,329,279 B2 2/2008 Haug et al.
7,331,993 B2 2/2008 White
7,374,560 B2 5/2008 Ressemann et al.
7,381,219 B2 6/2008 Salahieh et al.
7,381,220 B2 6/2008 Macoviak et al.
7,399,315 B2 7/2008 Iobbi
7,445,631 B2 11/2008 Salahieh et al.
7,470,285 B2 12/2008 Nugent et al.
7,491,232 B2 2/2009 Bolduc et al.
7,510,574 B2 3/2009 Lê et al.
7,524,330 B2 4/2009 Berreklouw
7,524,331 B2 4/2009 Birdsall et al.
7,530,995 B2 5/2009 Quijano et al.
7,544,206 B2 6/2009 Cohn
7,575,594 B2 8/2009 Sieracki
7,622,276 B2 11/2009 Cunanan et al.
7,628,803 B2 12/2009 Pavcnik et al.
7,632,298 B2 12/2009 Hijlkema et al.
7,641,687 B2 1/2010 Chinn et al.
7,670,370 B2 3/2010 Hill et al.
7,674,282 B2 3/2010 Wu et al.
7,712,606 B2 5/2010 Salahieh et al.
7,717,955 B2 5/2010 Lane et al.
7,722,638 B2 5/2010 Deyette et al.
7,722,662 B2 5/2010 Steinke et al.
7,722,666 B2 5/2010 Lafontaine
7,731,742 B2 6/2010 Schlick et al.
7,736,388 B2 6/2010 Goldfarb et al.
7,748,389 B2 7/2010 Salahieh et al.
7,758,625 B2 7/2010 Wu et al.
7,780,725 B2 8/2010 Haug et al.
7,799,065 B2 9/2010 Pappas
7,803,185 B2 9/2010 Gabbay
7,819,915 B2 10/2010 Stobie et al.
7,824,442 B2 11/2010 Salahieh et al.
7,824,443 B2 11/2010 Salahieh et al.
7,833,262 B2 11/2010 McGuckin et al.
7,846,204 B2 12/2010 Letac et al.
7,857,845 B2 12/2010 Stacchino et al.
7,892,281 B2 2/2011 Seguin et al.
7,892,292 B2 2/2011 Stack et al.
7,918,880 B2 4/2011 Austin
7,938,851 B2 5/2011 Olson et al.
7,959,666 B2 6/2011 Salahieh et al.
7,959,672 B2 6/2011 Salahieh et al.
7,988,724 B2 8/2011 Salahieh et al.
7,993,394 B2 8/2011 Hariton et al.
8,012,135 B2 9/2011 Dann et al.
8,029,564 B2 10/2011 Johnson et al.
8,048,153 B2 11/2011 Salahieh et al.
8,052,749 B2 11/2011 Salahieh et al.
8,075,611 B2 12/2011 Milwee et al.
8,136,659 B2 3/2012 Salahieh et al.
8,157,853 B2 4/2012 Laske et al.
8,163,014 B2 4/2012 Lane et al.
8,172,892 B2 5/2012 Chuter et al.
8,172,896 B2 5/2012 McNamara et al.
8,182,528 B2 5/2012 Salahieh et al.
8,192,351 B2 6/2012 Fishler et al.
8,226,710 B2 7/2012 Nguyen et al.
8,231,670 B2 7/2012 Salahieh et al.
8,236,049 B2 8/2012 Rowe et al.
8,246,678 B2 8/2012 Salahieh et al.
8,252,051 B2 8/2012 Chau et al.
8,252,052 B2 8/2012 Salahieh et al.
8,287,584 B2 10/2012 Salahieh et al.
8,308,798 B2 11/2012 Pintor et al.
8,317,858 B2 11/2012 Straubinger et al.
8,323,335 B2 12/2012 Rowe et al.
8,328,868 B2 12/2012 Paul et al.
8,343,213 B2 1/2013 Salahieh et al.
8,376,865 B2 2/2013 Forster et al.
8,377,117 B2 2/2013 Keidar et al.
8,398,708 B2 3/2013 Meiri et al.
8,403,983 B2 3/2013 Quadri et al.
8,414,644 B2 4/2013 Quadri et al.
8,579,962 B2 11/2013 Salahieh et al.
8,603,160 B2 12/2013 Salahieh et al.
8,617,236 B2 12/2013 Paul et al.
8,623,074 B2 1/2014 Ryan
8,623,076 B2 1/2014 Salahieh et al.
8,623,078 B2 1/2014 Salahieh et al.
8,668,733 B2 3/2014 Haug et al.
8,696,737 B2 4/2014 Gainor
8,696,743 B2 4/2014 Holecek et al.
8,788,020 B2 7/2014 Gregg et al.
8,828,078 B2 9/2014 Salahieh et al.
8,840,662 B2 9/2014 Salahieh et al.
8,840,663 B2 9/2014 Salahieh et al.
8,858,620 B2 10/2014 Salahieh et al.
8,894,703 B2 11/2014 Salahieh et al.
8,951,299 B2 2/2015 Paul et al.
8,992,608 B2 3/2015 Haug et al.
9,005,273 B2 4/2015 Salahieh et al.
9,011,521 B2 4/2015 Haug et al.
9,089,422 B2 * 7/2015 Ryan .................... A61F 2/2436
9,168,129 B2 10/2015 Valdez et al.
9,168,131 B2 10/2015 Yohanan et al.
9,675,451 B2 6/2017 Garde et al.
9,763,785 B2 9/2017 Styrc
9,895,225 B2 2/2018 Rolando et al.
9,974,649 B2 5/2018 Racchini et al.
11,439,732 B2 * 9/2022 Adamek-Bowers ........................ A61F 2/2418
2001/0002445 A1 5/2001 Vesely
2001/0007956 A1 7/2001 Letac et al.
2001/0010017 A1 7/2001 Letac et al.
2001/0021872 A1 9/2001 Bailey et al.
2001/0025196 A1 9/2001 Chinn et al.
2001/0027338 A1 10/2001 Greenberg
2001/0032013 A1 10/2001 Marton
2001/0039450 A1 11/2001 Pavcnik et al.
2001/0041928 A1 11/2001 Pavcnik et al.
2001/0041930 A1 11/2001 Globerman et al.
2001/0044634 A1 11/2001 Michael et al.
2001/0044652 A1 11/2001 Moore

(56) References Cited

U.S. PATENT DOCUMENTS

2001/0044656 A1 11/2001 Williamson et al.
2002/0002396 A1 1/2002 Fulkerson
2002/0010489 A1 1/2002 Grayzel et al.
2002/0026233 A1 2/2002 Shaknovich
2002/0029014 A1 3/2002 Jayaraman
2002/0029981 A1 3/2002 Nigam
2002/0032480 A1 3/2002 Spence et al.
2002/0032481 A1 3/2002 Gabbay
2002/0042651 A1 4/2002 Liddicoat et al.
2002/0052651 A1 5/2002 Myers et al.
2002/0055767 A1 5/2002 Forde et al.
2002/0055769 A1 5/2002 Wang
2002/0055774 A1 5/2002 Liddicoat
2002/0058987 A1 5/2002 Butaric et al.
2002/0058994 A1 5/2002 Hill et al.
2002/0058995 A1 5/2002 Stevens
2002/0077696 A1 6/2002 Zadno-Azizi et al.
2002/0077698 A1 6/2002 Peredo
2002/0082609 A1 6/2002 Green
2002/0095173 A1 7/2002 Mazzocchi et al.
2002/0095205 A1 7/2002 Edwin et al.
2002/0095209 A1 7/2002 Zadno-Azizi et al.
2002/0111674 A1 8/2002 Chouinard et al.
2002/0120328 A1 8/2002 Pathak et al.
2002/0123802 A1 9/2002 Snyders
2002/0138138 A1 9/2002 Yang
2002/0151970 A1 10/2002 Garrison et al.
2002/0156522 A1 10/2002 Ivancev et al.
2002/0161390 A1 10/2002 Mouw
2002/0161392 A1 10/2002 Dubrul
2002/0161394 A1 10/2002 Macoviak et al.
2002/0165576 A1 11/2002 Boyle et al.
2002/0177766 A1 11/2002 Mogul
2002/0183781 A1 12/2002 Casey et al.
2002/0188341 A1 12/2002 Elliott
2002/0188344 A1 12/2002 Bolea et al.
2002/0193871 A1 12/2002 Beyersdorf et al.
2003/0014104 A1 1/2003 Cribier
2003/0023303 A1 1/2003 Palmaz et al.
2003/0028247 A1 2/2003 Cali
2003/0036791 A1 2/2003 Philipp et al.
2003/0040736 A1 2/2003 Stevens et al.
2003/0040771 A1 2/2003 Hyodoh et al.
2003/0040772 A1 2/2003 Hyodoh et al.
2003/0040791 A1 2/2003 Oktay
2003/0040792 A1 2/2003 Gabbay
2003/0050694 A1 3/2003 Yang et al.
2003/0055495 A1 3/2003 Pease et al.
2003/0057156 A1 3/2003 Peterson et al.
2003/0060844 A1 3/2003 Borillo et al.
2003/0069492 A1 4/2003 Abrams et al.
2003/0069646 A1 4/2003 Stinson
2003/0070944 A1 4/2003 Nigam
2003/0074058 A1 4/2003 Sherry
2003/0093145 A1 5/2003 Lawrence-Brown et al.
2003/0100918 A1 5/2003 Duane
2003/0100919 A1 5/2003 Hopkins et al.
2003/0109924 A1 6/2003 Cribier
2003/0109930 A1 6/2003 Bluni et al.
2003/0114912 A1 6/2003 Sequin et al.
2003/0114913 A1 6/2003 Spenser et al.
2003/0114924 A1 6/2003 Moe
2003/0125795 A1 7/2003 Pavcnik et al.
2003/0130729 A1 7/2003 Paniagua et al.
2003/0135257 A1 7/2003 Taheri
2003/0144732 A1 7/2003 Cosgrove et al.
2003/0149475 A1 8/2003 Hyodoh et al.
2003/0149476 A1 8/2003 Damm et al.
2003/0149478 A1 8/2003 Figulla et al.
2003/0153974 A1 8/2003 Spenser et al.
2003/0165352 A1 9/2003 Ibrahim et al.
2003/0171803 A1 9/2003 Shimon
2003/0176884 A1 9/2003 Berrada et al.
2003/0181850 A1 9/2003 Diamond et al.
2003/0187495 A1 10/2003 Cully et al.
2003/0191516 A1 10/2003 Weldon et al.
2003/0195609 A1 10/2003 Berenstein et al.
2003/0195620 A1 10/2003 Huynh et al.
2003/0199759 A1 10/2003 Richard
2003/0199913 A1 10/2003 Dubrul et al.
2003/0199971 A1 10/2003 Tower et al.
2003/0199972 A1 10/2003 Zadno-Azizi et al.
2003/0204249 A1 10/2003 Letort
2003/0208224 A1 11/2003 Broome
2003/0212429 A1 11/2003 Keegan et al.
2003/0212452 A1 11/2003 Zadno-Azizi et al.
2003/0212454 A1 11/2003 Scott et al.
2003/0216774 A1 11/2003 Larson
2003/0225445 A1 12/2003 Derus et al.
2003/0229390 A1 12/2003 Ashton et al.
2003/0233117 A1 12/2003 Adams et al.
2003/0236567 A1 12/2003 Elliot
2004/0015232 A1 1/2004 Shu et al.
2004/0019374 A1 1/2004 Hojeibane et al.
2004/0030381 A1 2/2004 Shu
2004/0033364 A1 2/2004 Spiridigliozzi et al.
2004/0034411 A1 2/2004 Quijano et al.
2004/0039436 A1 2/2004 Spenser et al.
2004/0049224 A1 3/2004 Buehlmann et al.
2004/0049226 A1 3/2004 Keegan et al.
2004/0049262 A1 3/2004 Obermiller et al.
2004/0049266 A1 3/2004 Anduiza et al.
2004/0059409 A1 3/2004 Stenzel
2004/0073198 A1 4/2004 Gilson et al.
2004/0082904 A1 4/2004 Houde et al.
2004/0082967 A1 4/2004 Broome et al.
2004/0082989 A1 4/2004 Cook et al.
2004/0087982 A1 5/2004 Eskuri
2004/0088045 A1 5/2004 Cox
2004/0093016 A1 5/2004 Root et al.
2004/0093060 A1 5/2004 Seguin et al.
2004/0097788 A1 5/2004 Mourlas et al.
2004/0098022 A1 5/2004 Barone
2004/0098098 A1 5/2004 McGuckin et al.
2004/0098099 A1 5/2004 McCullagh et al.
2004/0098112 A1 5/2004 DiMatteo et al.
2004/0106990 A1 6/2004 Spence et al.
2004/0107004 A1 6/2004 Levine et al.
2004/0111096 A1 6/2004 Tu et al.
2004/0116951 A1 6/2004 Rosengart
2004/0116999 A1 6/2004 Ledergerber
2004/0117004 A1 6/2004 Osborne et al.
2004/0117009 A1 6/2004 Cali et al.
2004/0122468 A1 6/2004 Yodfat et al.
2004/0122516 A1 6/2004 Fogarty et al.
2004/0127936 A1 7/2004 Salahieh et al.
2004/0127979 A1 7/2004 Wilson et al.
2004/0133274 A1 7/2004 Webler et al.
2004/0138694 A1 7/2004 Tran et al.
2004/0138742 A1 7/2004 Myers et al.
2004/0138743 A1 7/2004 Myers et al.
2004/0148018 A1 7/2004 Carpentier et al.
2004/0148021 A1 7/2004 Cartledge et al.
2004/0153094 A1 8/2004 Dunfee et al.
2004/0158277 A1 8/2004 Lowe et al.
2004/0167565 A1 8/2004 Beulke et al.
2004/0167620 A1 8/2004 Ortiz et al.
2004/0181140 A1 9/2004 Falwell et al.
2004/0186558 A1 9/2004 Pavcnik et al.
2004/0186563 A1 9/2004 Lobbi
2004/0193261 A1 9/2004 Berreklouw
2004/0197695 A1 10/2004 Aono
2004/0199245 A1 10/2004 Lauterjung
2004/0204755 A1 10/2004 Robin
2004/0210304 A1 10/2004 Seguin et al.
2004/0210306 A1 10/2004 Quijano et al.
2004/0210307 A1 10/2004 Khairkhahan
2004/0215331 A1 10/2004 Chew et al.
2004/0215333 A1 10/2004 Duran et al.
2004/0215339 A1 10/2004 Drasler et al.
2004/0220655 A1 11/2004 Swanson et al.
2004/0225321 A1 11/2004 Krolik et al.
2004/0225353 A1 11/2004 McGuckin et al.
2004/0225354 A1 11/2004 Allen et al.

(56) References Cited

U.S. PATENT DOCUMENTS

2004/0225355 A1 11/2004 Stevens
2004/0243221 A1 12/2004 Fawzi et al.
2004/0254636 A1 12/2004 Flagle et al.
2004/0260390 A1 12/2004 Sarac et al.
2005/0010287 A1 1/2005 Macoviak et al.
2005/0021136 A1 1/2005 Xie et al.
2005/0033398 A1 2/2005 Seguin
2005/0033402 A1 2/2005 Cully et al.
2005/0043711 A1 2/2005 Corcoran et al.
2005/0043757 A1 2/2005 Arad et al.
2005/0043790 A1 2/2005 Seguin
2005/0049692 A1 3/2005 Numamoto et al.
2005/0049696 A1 3/2005 Siess et al.
2005/0055088 A1 3/2005 Liddicoat et al.
2005/0060016 A1 3/2005 Wu et al.
2005/0060029 A1 3/2005 Le et al.
2005/0065594 A1 3/2005 DiMatteo et al.
2005/0075584 A1 4/2005 Cali
2005/0075662 A1 4/2005 Pedersen et al.
2005/0075712 A1 4/2005 Biancucci et al.
2005/0075717 A1 4/2005 Nguyen et al.
2005/0075719 A1 4/2005 Bergheim
2005/0075724 A1 4/2005 Svanidze et al.
2005/0075730 A1 4/2005 Myers et al.
2005/0075731 A1 4/2005 Artof et al.
2005/0085841 A1 4/2005 Eversull et al.
2005/0085842 A1 4/2005 Eversull et al.
2005/0085843 A1 4/2005 Opolski et al.
2005/0085890 A1 4/2005 Rasmussen et al.
2005/0090846 A1 4/2005 Pedersen et al.
2005/0090890 A1 4/2005 Wu et al.
2005/0096692 A1 5/2005 Linder et al.
2005/0096734 A1 5/2005 Majercak et al.
2005/0096735 A1 5/2005 Hojeibane et al.
2005/0096736 A1 5/2005 Osse et al.
2005/0096738 A1 5/2005 Cali et al.
2005/0100580 A1 5/2005 Osborne et al.
2005/0107822 A1 5/2005 WasDyke
2005/0113910 A1 5/2005 Paniagua et al.
2005/0131438 A1 6/2005 Cohn
2005/0137683 A1 6/2005 Hezi-Yamit et al.
2005/0137686 A1 6/2005 Salahieh et al.
2005/0137687 A1 6/2005 Salahieh et al.
2005/0137688 A1 6/2005 Salahieh et al.
2005/0137689 A1 6/2005 Salahieh et al.
2005/0137690 A1 6/2005 Salahieh et al.
2005/0137691 A1 6/2005 Salahieh et al.
2005/0137692 A1 6/2005 Haug et al.
2005/0137693 A1 6/2005 Haug et al.
2005/0137694 A1 6/2005 Haug et al.
2005/0137695 A1 6/2005 Salahieh et al.
2005/0137696 A1 6/2005 Salahieh et al.
2005/0137697 A1 6/2005 Salahieh et al.
2005/0137698 A1 6/2005 Salahieh et al.
2005/0137699 A1 6/2005 Salahieh et al.
2005/0137701 A1 6/2005 Salahieh et al.
2005/0137702 A1 6/2005 Haug et al.
2005/0138689 A1 6/2005 Aukerman
2005/0143807 A1 6/2005 Pavcnik et al.
2005/0143809 A1 6/2005 Salahieh et al.
2005/0149159 A1 7/2005 Andreas et al.
2005/0165352 A1 7/2005 Henry et al.
2005/0165477 A1 7/2005 Anduiza et al.
2005/0165479 A1 7/2005 Drews et al.
2005/0182486 A1 8/2005 Gabbay
2005/0197694 A1 9/2005 Pai et al.
2005/0197695 A1 9/2005 Stacchino et al.
2005/0203549 A1 9/2005 Realyvasquez
2005/0203614 A1 9/2005 Forster et al.
2005/0203615 A1 9/2005 Forster et al.
2005/0203616 A1 9/2005 Cribier
2005/0203617 A1 9/2005 Forster et al.
2005/0203618 A1 9/2005 Sharkawy et al.
2005/0203818 A9 9/2005 Rotman et al.
2005/0209580 A1 9/2005 Freyman
2005/0228472 A1 10/2005 Case et al.
2005/0228495 A1 10/2005 Macoviak
2005/0234546 A1 10/2005 Nugent et al.
2005/0240200 A1 10/2005 Bergheim
2005/0240262 A1 10/2005 White
2005/0251250 A1 11/2005 Verhoeven et al.
2005/0251251 A1 11/2005 Cribier
2005/0261759 A1 11/2005 Lambrecht et al.
2005/0267560 A1 12/2005 Bates
2005/0283231 A1 12/2005 Haug et al.
2005/0283962 A1 12/2005 Boudjemline
2006/0004439 A1 1/2006 Spenser et al.
2006/0004442 A1 1/2006 Spenser et al.
2006/0015168 A1 1/2006 Gunderson
2006/0025854 A1 2/2006 Ashinski et al.
2006/0025855 A1 2/2006 Lashinski et al.
2006/0025857 A1 2/2006 Bergheim et al.
2006/0058872 A1 3/2006 Salahieh et al.
2006/0149360 A1 7/2006 Schwammenthal et al.
2006/0155312 A1 7/2006 Levine et al.
2006/0161249 A1 7/2006 Realyvasquez et al.
2006/0173524 A1 8/2006 Salahieh et al.
2006/0195183 A1 8/2006 Navia et al.
2006/0195184 A1 8/2006 Lane et al.
2006/0195185 A1 8/2006 Lane et al.
2006/0253191 A1 11/2006 Salahieh et al.
2006/0259134 A1 11/2006 Schwammenthal et al.
2006/0259137 A1 11/2006 Artof et al.
2006/0271166 A1 11/2006 Thill et al.
2006/0271172 A1 11/2006 Tehrani
2006/0287668 A1 12/2006 Fawzi et al.
2006/0287717 A1 12/2006 Rowe et al.
2007/0010876 A1 1/2007 Salahieh et al.
2007/0010877 A1 1/2007 Salahieh et al.
2007/0016286 A1 1/2007 Herrmann et al.
2007/0018214 A1 1/2007 Ahn et al.
2007/0027535 A1 2/2007 Purdy, Jr. et al.
2007/0055340 A1 3/2007 Pryor
2007/0061008 A1 3/2007 Salahieh et al.
2007/0112355 A1 5/2007 Salahieh et al.
2007/0118214 A1 5/2007 Salahieh et al.
2007/0129795 A1 6/2007 Hill et al.
2007/0162107 A1 7/2007 Haug et al.
2007/0173918 A1 7/2007 Dreher et al.
2007/0203503 A1 8/2007 Salahieh et al.
2007/0244552 A1 10/2007 Salahieh et al.
2007/0282436 A1 12/2007 Pinchuk
2007/0288089 A1 12/2007 Gurskis et al.
2008/0009940 A1 1/2008 Cribier
2008/0033541 A1 2/2008 Gelbart et al.
2008/0033543 A1 2/2008 Gurskis et al.
2008/0071363 A1 3/2008 Tuval et al.
2008/0082165 A1 4/2008 Wilson et al.
2008/0125859 A1 5/2008 Salahieh et al.
2008/0188928 A1 8/2008 Salahieh et al.
2008/0208328 A1 8/2008 Antocci et al.
2008/0208332 A1 8/2008 Lamphere et al.
2008/0221672 A1 9/2008 Lamphere et al.
2008/0234814 A1 9/2008 Salahieh et al.
2008/0255661 A1 10/2008 Straubinger et al.
2008/0269878 A1 10/2008 Iobbi
2008/0275540 A1 11/2008 Wen
2008/0288054 A1 11/2008 Pulnev et al.
2009/0005863 A1 1/2009 Goetz et al.
2009/0030512 A1 1/2009 Thielen et al.
2009/0054969 A1 2/2009 Salahieh et al.
2009/0076598 A1 3/2009 Salahieh et al.
2009/0093877 A1 4/2009 Keidar et al.
2009/0171456 A1 7/2009 Kveen et al.
2009/0216312 A1 8/2009 Straubinger et al.
2009/0222076 A1 9/2009 Figulla et al.
2009/0240320 A1 9/2009 Tuval et al.
2009/0264759 A1 10/2009 Byrd
2009/0264997 A1 10/2009 Salahieh et al.
2009/0299462 A1 12/2009 Fawzi et al.
2010/0023120 A1 1/2010 Holecek et al.
2010/0036479 A1 2/2010 Hill et al.
2010/0036484 A1 2/2010 Hariton et al.
2010/0049313 A1 2/2010 Alon et al.

(56) References Cited

U.S. PATENT DOCUMENTS

2010/0082089 A1 4/2010 Quadri et al.
2010/0082094 A1 4/2010 Quadri et al.
2010/0094399 A1 4/2010 Dorn et al.
2010/0100176 A1 4/2010 Elizondo et al.
2010/0121434 A1 5/2010 Paul et al.
2010/0131054 A1 5/2010 Tuval et al.
2010/0161045 A1 6/2010 Righini
2010/0168844 A1 7/2010 Toomes et al.
2010/0185275 A1 7/2010 Richter et al.
2010/0191320 A1 7/2010 Straubinger et al.
2010/0191326 A1 7/2010 Alkhatib
2010/0191327 A1 7/2010 Lane et al.
2010/0219092 A1 9/2010 Salahieh et al.
2010/0249894 A1 9/2010 Oba et al.
2010/0249908 A1 9/2010 Chau et al.
2010/0249915 A1 9/2010 Zhang
2010/0249916 A1 9/2010 Zhang
2010/0249917 A1 9/2010 Zhang
2010/0249918 A1 9/2010 Zhang
2010/0256752 A1 10/2010 Forster et al.
2010/0262231 A1 10/2010 Tuval et al.
2010/0280495 A1 11/2010 Paul et al.
2010/0298931 A1 11/2010 Quadri et al.
2011/0000073 A1 1/2011 O'Fallon et al.
2011/0098802 A1 4/2011 Braido et al.
2011/0125258 A1 5/2011 Centola
2011/0166648 A1 7/2011 Robin et al.
2011/0172765 A1 7/2011 Nguyen et al.
2011/0213460 A1 9/2011 Lashinski et al.
2011/0218619 A1 9/2011 Benichou et al.
2011/0224781 A1 9/2011 White
2011/0230956 A1 9/2011 White
2011/0245918 A1 10/2011 White
2011/0257735 A1 10/2011 Salahieh et al.
2011/0264196 A1 10/2011 Savage et al.
2011/0276128 A1 11/2011 Cao et al.
2011/0276129 A1 11/2011 Salahieh et al.
2011/0288634 A1 11/2011 Tuval et al.
2011/0295363 A1 12/2011 Girard et al.
2011/0319991 A1 12/2011 Hariton et al.
2012/0016469 A1 1/2012 Salahieh et al.
2012/0016471 A1 1/2012 Salahieh et al.
2012/0022629 A1 1/2012 Perera et al.
2012/0022642 A1 1/2012 Haug et al.
2012/0029627 A1 2/2012 Salahieh et al.
2012/0041549 A1 2/2012 Salahieh et al.
2012/0041550 A1 2/2012 Salahieh et al.
2012/0046740 A1 2/2012 Paul et al.
2012/0053683 A1 3/2012 Salahieh et al.
2012/0059454 A1 3/2012 Millwee et al.
2012/0078356 A1 3/2012 Fish et al.
2012/0078357 A1 3/2012 Conklin
2012/0089224 A1 4/2012 Haug et al.
2012/0095549 A1 4/2012 Forster et al.
2012/0101567 A1 4/2012 Jansen
2012/0123529 A1 5/2012 Levi et al.
2012/0132547 A1 5/2012 Salahieh et al.
2012/0136432 A1 5/2012 Forster et al.
2012/0143316 A1 6/2012 Seguin et al.
2012/0179244 A1 7/2012 Schankereli et al.
2012/0185039 A1 7/2012 Tuval et al.
2012/0197379 A1 8/2012 Laske et al.
2012/0226348 A1 9/2012 Lane et al.
2012/0232459 A1 9/2012 Dann et al.
2012/0245706 A1 9/2012 Alavi et al.
2012/0259409 A1 10/2012 Nguyen et al.
2012/0303113 A1 11/2012 Benichou et al.
2012/0303116 A1 11/2012 Gorman et al.
2012/0330409 A1 12/2012 Haug et al.
2013/0013057 A1 1/2013 Salahieh et al.
2013/0018457 A1 1/2013 Gregg et al.
2013/0030520 A1 1/2013 Lee et al.
2013/0079867 A1 3/2013 Hoffman et al.
2013/0079869 A1 3/2013 Straubinger et al.
2013/0090729 A1 4/2013 Gregg et al.
2013/0096664 A1 4/2013 Goetz et al.
2013/0116778 A1 5/2013 Gregg et al.
2013/0123796 A1 5/2013 Sutton et al.
2013/0138207 A1 5/2013 Quadri et al.
2013/0158656 A1 6/2013 Sutton et al.
2013/0184813 A1 7/2013 Quadri et al.
2013/0190865 A1 7/2013 Anderson
2013/0304199 A1 11/2013 Sutton et al.
2014/0000112 A1 1/2014 Braido et al.
2014/0005772 A1 1/2014 Edelman et al.
2014/0018911 A1 1/2014 Zhou et al.
2014/0094904 A1 4/2014 Salahieh et al.
2014/0114405 A1 4/2014 Paul et al.
2014/0114406 A1 4/2014 Salahieh et al.
2014/0121766 A1 5/2014 Salahieh et al.
2014/0135912 A1 5/2014 Salahieh et al.
2014/0172077 A1 6/2014 Bruchman et al.
2014/0243966 A1 8/2014 Garde et al.
2014/0243967 A1 8/2014 Salahieh et al.
2014/0277417 A1 9/2014 Schraut et al.
2014/0277423 A1 9/2014 Alkhatib et al.
2015/0005863 A1 1/2015 Para
2015/0012085 A1 1/2015 Salahieh et al.
2015/0073540 A1 3/2015 Salahieh et al.
2015/0073541 A1 3/2015 Salahieh et al.
2015/0127094 A1 5/2015 Salahieh et al.
2015/0142104 A1 5/2015 Braido
2015/0157455 A1 6/2015 Hoang et al.
2015/0320552 A1 11/2015 Letac et al.
2015/0320556 A1 11/2015 Levi et al.
2016/0045307 A1 2/2016 Yohanan et al.
2016/0199184 A1 7/2016 Ma et al.
2017/0042672 A1 2/2017 Backus et al.
2017/0049566 A1 2/2017 Zeng et al.
2017/0333183 A1* 11/2017 Backus ................. A61F 2/2436

FOREIGN PATENT DOCUMENTS

CN 1338951 A 3/2002
DE 19532846 A1 3/1997
DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
EP 0103546 B1 5/1988
EP 0144167 B1 11/1989
EP 579523 A1 1/1994
EP 0409929 B1 4/1997
EP 0850607 A1 7/1998
EP 0597967 B1 12/1999
EP 1000590 A1 5/2000
EP 1057459 A1 12/2000
EP 1057460 A1 12/2000
EP 1078610 A2 2/2001
EP 1088529 A2 4/2001
EP 0937439 B1 9/2003
EP 1340473 A2 9/2003
EP 1356793 A3 3/2004
EP 1042045 B1 5/2004
EP 0819013 B1 6/2004
EP 1430853 A2 6/2004
EP 1435879 A1 7/2004
EP 1439800 A2 7/2004
EP 1469797 A1 10/2004
EP 1472996 A1 11/2004
EP 1229864 B1 4/2005
EP 1059894 B1 7/2005
EP 1551274 A2 7/2005
EP 1551336 A1 7/2005
EP 1562515 A1 8/2005
EP 1570809 A1 9/2005
EP 1576937 A2 9/2005
EP 1582178 A2 10/2005
EP 1582179 A2 10/2005
EP 1589902 A1 11/2005
EP 1600121 A1 11/2005

(56) References Cited

FOREIGN PATENT DOCUMENTS

| | | | |
|---|---|---|---|
| EP | 1156757 | B1 | 12/2005 |
| EP | 1616531 | A2 | 1/2006 |
| EP | 1605871 | B1 | 7/2008 |
| EP | 2119417 | A2 | 11/2009 |
| EP | 2749254 | B1 | 6/2015 |
| EP | 2898858 | A1 | 7/2015 |
| EP | 2926766 | A1 | 10/2015 |
| FR | 2788217 | A1 | 7/2000 |
| GB | 2056023 | A | 3/1981 |
| GB | 2398245 | A | 8/2004 |
| JP | 2006333940 | A | 12/2006 |
| SU | 1271508 | A1 | 11/1986 |
| SU | 1371700 | A1 | 2/1988 |
| WO | 9117720 | A1 | 11/1991 |
| WO | 9217118 | A1 | 10/1992 |
| WO | 9301768 | A1 | 2/1993 |
| WO | 9315693 | A1 | 8/1993 |
| WO | 9504556 | A2 | 2/1995 |
| WO | 9529640 | A1 | 11/1995 |
| WO | 9614032 | A1 | 5/1996 |
| WO | 9624306 | A1 | 8/1996 |
| WO | 9640012 | A1 | 12/1996 |
| WO | 9721403 | A1 | 6/1997 |
| WO | 9748350 | A1 | 12/1997 |
| WO | 9829057 | A1 | 7/1998 |
| WO | 9836790 | A1 | 8/1998 |
| WO | 9850103 | A1 | 11/1998 |
| WO | 9855047 | A1 | 12/1998 |
| WO | 9857599 | A2 | 12/1998 |
| WO | 9933414 | A1 | 7/1999 |
| WO | 9940964 | A1 | 8/1999 |
| WO | 9944542 | A2 | 9/1999 |
| WO | 9947075 | A1 | 9/1999 |
| WO | 9951165 | A1 | 10/1999 |
| WO | 0009059 | A2 | 2/2000 |
| WO | 2000009059 | A2 | 2/2000 |
| WO | 0041652 | A1 | 7/2000 |
| WO | 0044308 | A2 | 8/2000 |
| WO | 0044311 | A2 | 8/2000 |
| WO | 0044313 | A1 | 8/2000 |
| WO | 0045874 | A1 | 8/2000 |
| WO | 0047139 | A1 | 8/2000 |
| WO | 0049970 | A1 | 8/2000 |
| WO | 0067661 | A2 | 11/2000 |
| WO | 0105331 | A1 | 1/2001 |
| WO | 0106958 | A1 | 2/2001 |
| WO | 0106959 | A1 | 2/2001 |
| WO | 0108596 | A1 | 2/2001 |
| WO | 0110320 | A1 | 2/2001 |
| WO | 0110343 | A1 | 2/2001 |
| WO | 0135870 | A1 | 5/2001 |
| WO | 0149213 | A2 | 7/2001 |
| WO | 0154625 | A1 | 8/2001 |
| WO | 0162189 | A1 | 8/2001 |
| WO | 2001054625 | A1 | 8/2001 |
| WO | 0164137 | A1 | 9/2001 |
| WO | 0176510 | A2 | 10/2001 |
| WO | 0197715 | A1 | 12/2001 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 02056955 | A1 | 7/2002 |
| WO | 02069842 | A2 | 9/2002 |
| WO | 02100297 | A2 | 12/2002 |
| WO | 03003943 | A2 | 1/2003 |
| WO | 03003949 | A2 | 1/2003 |
| WO | 03011195 | A2 | 2/2003 |
| WO | 03015851 | A1 | 2/2003 |
| WO | 03028592 | A1 | 4/2003 |
| WO | 03030776 | A2 | 4/2003 |
| WO | 03032869 | A1 | 4/2003 |
| WO | 03037222 | A2 | 5/2003 |
| WO | 03037227 | A2 | 5/2003 |
| WO | 03047468 | A1 | 6/2003 |
| WO | 03047648 | A2 | 6/2003 |
| WO | 03088873 | A1 | 10/2003 |
| WO | 03094793 | A1 | 11/2003 |
| WO | 03094797 | A1 | 11/2003 |
| WO | 03096932 | A1 | 11/2003 |
| WO | 2004006803 | A1 | 1/2004 |
| WO | 2004006804 | A1 | 1/2004 |
| WO | 2004014256 | A1 | 2/2004 |
| WO | 2004019817 | A1 | 3/2004 |
| WO | 2004021922 | A2 | 3/2004 |
| WO | 2004023980 | A2 | 3/2004 |
| WO | 2004019811 | A9 | 4/2004 |
| WO | 2004026117 | A2 | 4/2004 |
| WO | 2004041126 | A1 | 5/2004 |
| WO | 2004043293 | A2 | 5/2004 |
| WO | 2004047681 | A1 | 6/2004 |
| WO | 2004058106 | A2 | 8/2004 |
| WO | 2004066876 | A1 | 8/2004 |
| WO | 2004082536 | A1 | 9/2004 |
| WO | 2004089250 | A1 | 10/2004 |
| WO | 2004089253 | A1 | 10/2004 |
| WO | 2004093728 | A2 | 11/2004 |
| WO | 2004105651 | A1 | 12/2004 |
| WO | 2005002466 | A2 | 1/2005 |
| WO | 2005004753 | A1 | 1/2005 |
| WO | 2005009285 | A2 | 2/2005 |
| WO | 2005011534 | A1 | 2/2005 |
| WO | 2005011535 | A2 | 2/2005 |
| WO | 2005023155 | A1 | 3/2005 |
| WO | 2005027790 | A1 | 3/2005 |
| WO | 2005046528 | A1 | 5/2005 |
| WO | 2005046529 | A1 | 5/2005 |
| WO | 2005048883 | A1 | 6/2005 |
| WO | 2005065585 | A1 | 7/2005 |
| WO | 2005084595 | A1 | 9/2005 |
| WO | 2005087140 | A1 | 9/2005 |
| WO | 2005096993 | A1 | 10/2005 |
| WO | 2006005015 | A2 | 1/2006 |
| WO | 2006009690 | A1 | 1/2006 |
| WO | 2006027499 | A2 | 3/2006 |
| WO | 2005062980 | A3 | 5/2006 |
| WO | 2006127412 | A1 | 11/2006 |
| WO | 2007028052 | A | 3/2007 |
| WO | 2007035471 | A2 | 3/2007 |
| WO | 2005102015 | A3 | 4/2007 |
| WO | 2006138391 | A2 | 4/2007 |
| WO | 2007044285 | A2 | 4/2007 |
| WO | 2007058847 | A2 | 5/2007 |
| WO | 2007092354 | A2 | 8/2007 |
| WO | 2007097983 | A2 | 8/2007 |
| WO | 2007053243 | A2 | 9/2007 |
| WO | 2007033093 | A2 | 1/2008 |
| WO | 2010042950 | A2 | 4/2010 |
| WO | 2010098857 | A1 | 9/2010 |
| WO | 2012116368 | A2 | 8/2012 |
| WO | 2012162228 | A1 | 11/2012 |
| WO | 2013009975 | A1 | 1/2013 |
| WO | 2013012801 | A2 | 1/2013 |
| WO | 2013028387 | A2 | 2/2013 |
| WO | 2013074671 | A1 | 5/2013 |
| WO | 2013096545 | A1 | 6/2013 |
| WO | 2014008207 | A1 | 1/2014 |
| WO | 2015152980 | A1 | 10/2015 |
| WO | 2016126511 | A2 | 8/2016 |
| WO | 2016126524 | A1 | 8/2016 |
| WO | 2016164209 | A1 | 10/2016 |
| WO | 2017027289 | A1 | 2/2017 |
| WO | 2017189671 | A1 | 11/2017 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Knudsen et al., “Catheter-implanted prosthetic heart valves.” Int’l J. of Art. Organs, 16(5): 253-262, May 1993.

(56) References Cited

OTHER PUBLICATIONS

Kort et al., "Minimally Invasive Aortic Valve Replacement: Echocardiographic and Clinical Results." Am. Heart J., 142(3): 476-481, Sep. 2001.
Lawrence et al., "Percutaneous Endovascular Graft: Experimental Evaluation," Radiology, 163(2): 357-60 (May (1987).
Levi et al., "Future of Interventional Cardiology in Pediactrics." Current Opinion in Cardiol., 18:79-90 (2003).
Levy, "*Mycobacterium chelonei* Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
Mckay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," ASAIO J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5(6):491-9 (1991).
Pavcnik et al., "Percutaneous Bioprosthetic Venous Valve: A Long-term Study in Sheep." J. of Vascular Surg., 35(3):698-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. Apr. 1999.
U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al,. "Stent Attachment Site-related Endoleakage after Stent Graft Treatment: An in vitro study of the effects of graft size, stent type, and atherosclerotic wall changes." J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).
Stassano, "Mid-term Results of the Valve-on-Valve Technique for Bioprosthetic Failure." European Journal of Cardiothoracic Surgery: vol. 18, 453-457, Oct. 2000.
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, Aug. 19, 2011.
Supplemental Search Report from EP Patent Office, EP Application No. 05758878.2, Oct. 24, 2011.
Textbook of Interventional Cardiology, 2d Ed., Chapter 75: Percutaneous Expandable Prosthetic Valves (1994).
Thompson et al., "Endoluminal stent grafting of the thoracic aorta: Initial experience with the Gore Excluder," Journal of Vascular Surgery, 1163-70 (Jun. 2002).
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
USPTO Case IPR2016-___, U.S. Pat. No. 8,992,608 "Petition for Interpartes Review of U.S. Pat. No. 8,992,608" Oct. 12, 2016.
USPTO Case IPR 2017-0006, U.S. Pat. No. 8,992,608 B2, "Final Written Decision" Mar. 23, 2018.
Fluency Vascular Stent Graft Instructions for Use (2003).
Invite to Pay Additional Fees And, Where Applicable, Protest Fee, PCT/US2016/045335, mailed Nov. 14, 2016.
International Search Report and Written Opinion dated Aug. 16, 2017 for International Application No. PCT/US2017/033160.
International Search Report and Written Opinion, PCT/US2016/045323, mailed Feb. 2, 2017.
International Search Report and Written Opinion dated Jul. 11, 2017 for International Application No. PCT/US2017/029552.
Martin et al., "A radiopaque electrospun scaffold for engineering fibrous musculoskelatal tissues: scaffold characterization an in vivo applications." Acta Biomater , (26): 20 pages, Oct. 15, 2015.
International Search Report and Written Opinion dated May 21, 2019 for International Application No. PCT/US2019/019479.
Carpentier-Edwards Perimount Bioprosthesis (2003).
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC,

(56) References Cited

OTHER PUBLICATIONS v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent—Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Potter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, mailed Aug. 10, 2011.
Examiner's First Report on AU Patent Application No. 2011202667, issued on May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).

* cited by examiner

EMBEDDED RADIOPAQUE MARKER IN ADAPTIVE SEAL

CROSS-REFERENCE TO RELATED APPLICATIONS

This application is a continuation of U.S. application Ser. No. 16/285,337, filed Feb. 26, 2019, which claims the benefit of priority under 35 U.S.C. § 119 to U.S. Provisional Application Ser. No. 62/635,236, filed Feb. 26, 2018, the entirety of which is incorporated herein by reference.

TECHNICAL FIELD

The present disclosure pertains to medical devices and methods for manufacturing and/or using medical devices. More particularly, the present disclosure pertains to configurations of a replacement heart valve implant.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a seal member for use with a replacement heart valve implant may comprise a tubular polymeric seal element configured to be disposed on an outer surface of a replacement heart valve implant, the tubular polymeric seal element defining a central longitudinal axis; and a reinforcement strip fixedly attached to the tubular polymeric seal element proximate a first end of the tubular polymeric seal element, the reinforcement strip extending circumferentially around the central longitudinal axis. The reinforcement strip may include a radiopaque element extending circumferentially around the central longitudinal axis.

In addition or alternatively, and in a second aspect, the radiopaque element is at least partially embedded in the reinforcement strip.

In addition or alternatively, and in a third aspect, radiopaque element includes a polyurethane spray coating doped with radiopaque nanoparticles.

In addition or alternatively, and in a fourth aspect, the polyurethane spray coating is disposed on the reinforcement strip.

In addition or alternatively, and in a fifth aspect, the polyurethane spray coating is intermingled with the reinforcement strip.

In addition or alternatively, and in a sixth aspect, the radiopaque nanoparticles include one or more of the following: tungsten, platinum, tantalum, cobalt, chromium, nickel, titanium, gold, and palladium.

In addition or alternatively, and in a seventh aspect, the reinforcement strip is formed from an electrospun polyester matrix doped with radiopaque nanoparticles.

In addition or alternatively, and in an eighth aspect, the reinforcement strip is formed from a chopped radiopaque fiber-polyurethane matrix.

In addition or alternatively, and in a ninth aspect, a replacement heart valve implant may comprise a tubular metallic support structure defining a central longitudinal axis; a plurality of valve leaflets disposed within the tubular metallic support structure; and a seal member comprising a tubular polymeric seal element disposed on an outer surface of the tubular metallic support structure and a reinforcement strip fixedly attached to the tubular polymeric seal element proximate a first end of the tubular polymeric seal element, the reinforcement strip extending circumferentially around the central longitudinal axis at an inflow end of the tubular metallic support structure. The reinforcement strip may include a radiopaque element extending circumferentially around the central longitudinal axis.

In addition or alternatively, and in a tenth aspect, the reinforcement strip is fixedly attached to the inflow end of the tubular metallic support structure.

In addition or alternatively, and in an eleventh aspect, the tubular metallic support structure is configured to shift between a collapsed delivery configuration and an expanded deployed configuration.

In addition or alternatively, and in a twelfth aspect, an overall length of the tubular metallic support structure in the expanded deployed configuration is less than in the collapsed delivery configuration.

In addition or alternatively, and in a thirteenth aspect, the seal member is configured to engage and seal against an annulus of a native heart valve in the expanded deployed configuration.

In addition or alternatively, and in a fourteenth aspect, the reinforcement strip includes a scalloped downstream edge.

In addition or alternatively, and in a fifteenth aspect, the radiopaque element extends completely around the central longitudinal axis.

In addition or alternatively, and in a sixteenth aspect, a method of locating a replacement heart valve implant during an implantation procedure may comprise advancing the replacement heart valve implant through a vasculature toward a native heart valve in a delivery configuration, the replacement heart valve implant comprising an expandable tubular support structure defining a central longitudinal axis, a plurality of valve leaflets disposed within the tubular support structure, and a seal member comprising: a tubular polymeric seal element disposed on an outer surface of the tubular support structure and a reinforcement strip fixedly attached to the tubular polymeric seal element proximate a first end of the tubular polymeric seal element, the reinforcement strip extending circumferentially around the central longitudinal axis at an inflow end of the tubular support structure. The reinforcement strip may include a radiopaque element extending circumferentially around the central longitudinal axis in a first plane. The method may further comprise imaging the replacement heart valve implant within the vasculature and the native heart valve concurrently as the replacement heart valve implant approaches the native heart valve, wherein the imaging identifies a reference plane extending through an annulus of the native heart valve generally perpendicular to a direction of fluid flow through the native heart valve; and expanding the tubular support structure within the native heart valve with the first plane positioned substantially parallel to the reference plane and offset less than 4 mm from the reference plane.

In addition or alternatively, and in a seventeenth aspect, the first plane is offset less than 2 mm from the reference plane.

In addition or alternatively, and in an eighteenth aspect, the first plane is positioned substantially coplanar with the reference plane.

In addition or alternatively, and in a nineteenth aspect, the radiopaque element includes radiopaque nanoparticles embedded in the reinforcement strip.

In addition or alternatively, and in a twentieth aspect, the reinforcement strip is fixedly attached to tubular support structure at the inflow end.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
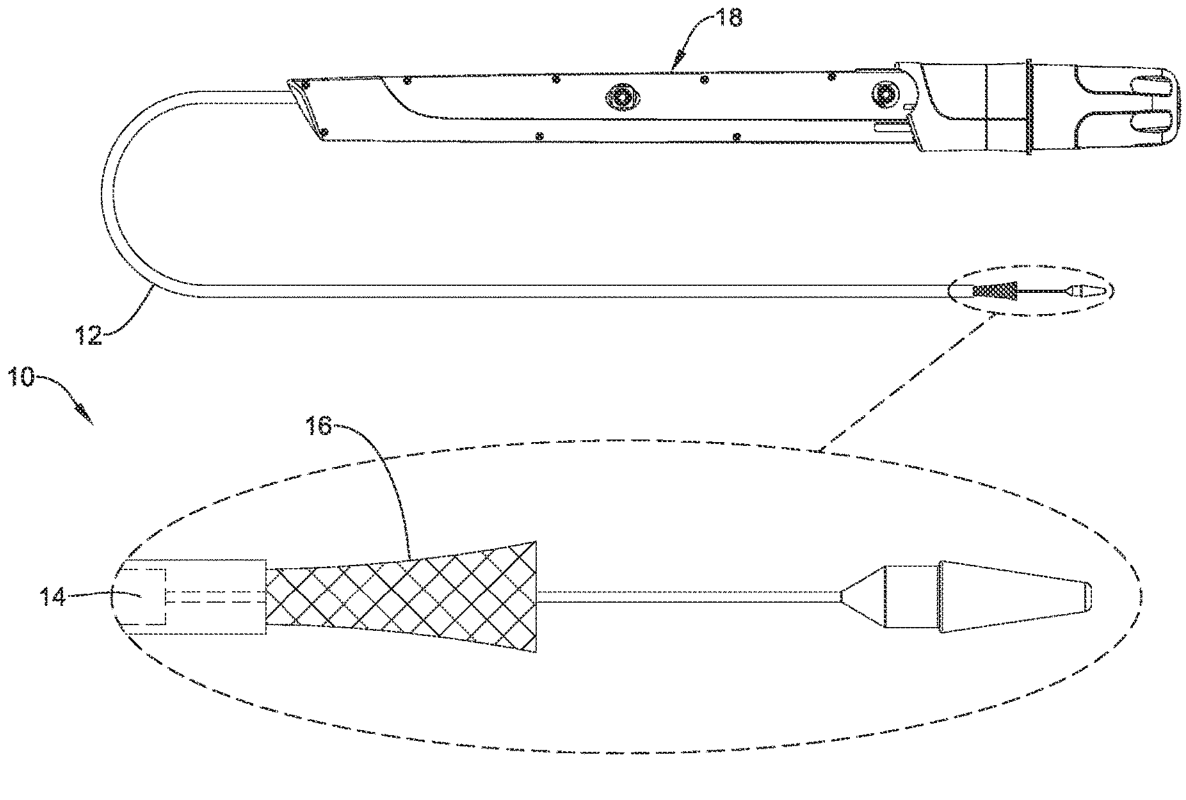
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide other desirable features and/or benefits as described herein.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices and/or implants to one or more locations within the anatomy. In at least some embodiments, the medical device system 10 may include a replacement heart valve delivery system (e.g., a replacement aortic valve delivery system) that can be used for percutaneous delivery of a replacement heart valve implant 16 (e.g. a replacement mitral valve, a replacement aortic valve, etc.) to an area of interest in the anatomy, such as a native heart valve. This, however, is not intended to be limiting as the medical device system 10 may also be used for other interventions including valve repair, valvuloplasty, and the like, or other similar interventions.

FIG. 1 illustrates the medical device system 10 including the replacement heart valve implant 16 configured to be disposed within the area of interest, such as a native heart valve (e.g., a mitral valve, an aortic valve, etc.), wherein the replacement heart valve implant 16 may be disposed within a lumen of the medical device system 10 in a delivery configuration for delivery to the area of interest. Upon delivery to the area of interest, the replacement heart valve implant 16 may be shifted to a deployed configuration. In some embodiments, the medical device system 10 may include an outer sheath 12 having a lumen extending from a proximal portion and/or proximal end of the outer sheath 12 to a distal end of the outer sheath 12. The replacement heart valve implant 16 may be disposed within the lumen of the outer sheath 12 proximate the distal end of the outer sheath 12 in the delivery configuration. In some embodiments, the medical device system 10 may include a handle 18 disposed proximate and/or at the proximal end of the outer sheath 12.

The medical device system 10 may include an inner sheath or catheter 14 disposed within the lumen of the outer sheath 12 and/or slidable with respect to the outer sheath 12 within the lumen of the outer sheath 12. In some embodiments, the handle 18 may be disposed proximate and/or at a proximal end of the inner sheath or catheter 14. In some embodiments, the inner sheath or catheter 14 may be a tubular structure having one or more lumens extending therethrough, the inner sheath or catheter 14 may be a solid shaft, or the inner sheath or catheter 14 may be a combination thereof. In some embodiments, the medical device system 10 may include an actuator element releasably connecting the replacement heart valve implant 16 to the handle 18. For example, the actuator element may extend from the handle 18 to the replacement heart valve implant 16, the replacement heart valve implant 16 being disposed at a distal end of the lumen of the outer sheath 12. The actuator element may extend distally from the inner sheath or catheter 14 to the replacement heart valve implant 16. In some embodiments, the actuator element may be slidably disposed within and/or may extend slidably through the inner sheath or catheter 14.

The handle 18 and/or the actuator element may be configured to manipulate the position of the outer sheath 12 relative to the inner sheath or catheter 14 and/or aid in the deployment of the replacement heart valve implant 16. For example, the inner sheath or catheter 14 and/or the actuator element may be used to move the replacement heart valve implant 16 with respect to the outer sheath 12 of the medical device system 10. In some embodiments, the inner sheath or catheter 14 and/or the actuator element may be advanced distally within the lumen of the outer sheath 12 to push the replacement heart valve implant 16 out the distal end of the outer sheath 12 and/or the medical device system 10 to deploy the replacement heart valve implant 16 within the area of interest (e.g., the native heart valve, etc.). Alternatively, the inner sheath or catheter 14 and/or the actuator element may be held in a fixed position relative to the replacement heart valve implant 16 and the outer sheath 12 may be withdrawn proximally relative to the inner sheath or catheter 14, the actuator element, and/or the replacement heart valve implant 16 to deploy the replacement heart valve implant 16 within the area of interest (e.g., the native heart valve, etc.).

In some embodiments, the medical device system 10 may include a nose cone disposed at a distal end of a guidewire extension tube, wherein the guidewire extension tube may extend distally from the inner sheath or catheter 14 and/or the outer sheath 12. In at least some embodiments, the nose cone may be designed to have an atraumatic shape and/or may include a ridge or ledge that is configured to abut a distal end of the outer sheath 12 during delivery of the replacement heart valve implant 16. Some examples of suitable but non-limiting materials for the medical device system 10, the outer sheath 12, the inner sheath or catheter 14, the handle 18, the actuator element, the nose cone, etc. and/or components or elements thereof, are described below.

In use, the medical device system 10 may be advanced percutaneously through the vasculature to the area of interest. For example, the medical device system 10 may be advanced through the vasculature and across the aortic arch to a defective native heart valve (e.g., aortic valve, mitral valve, etc.). Alternative approaches to treat a defective native heart valve are also contemplated with the medical device system 10. During delivery, the replacement heart valve implant 16 may be generally disposed in an elongated and low profile "delivery" configuration within the lumen of the outer sheath 12. Once positioned at the area of interest, the outer sheath 12 may be retracted relative to the replacement heart valve implant 16 to expose the replacement heart valve implant 16. In at least some embodiments, the replacement heart valve implant 16 may be disposed in an "everted" configuration or a partially-everted configuration while disposed within the lumen of the outer sheath 12 and/or immediately upon exposure after retracting the outer sheath 12. In some embodiments, the replacement heart valve implant 16 may be everted in the "delivery" configuration. The "everted" configuration may involve at least a portion of the valve leaflets (discussed below) of the replacement heart valve implant 16 being disposed outside of the expandable anchor member (discussed below) of the replacement heart valve implant 16 during delivery, thereby permitting a smaller radial profile of the replacement heart valve implant 16 and the use of a smaller overall profile of the outer sheath 12 and/or the medical device system 10. In some embodiments, the "delivery" configuration and the "everted" configuration may be substantially similar and/or may be used interchangeably herein.

The replacement heart valve implant 16 may be actuated using the handle 18 and/or the actuator element in order to translate the replacement heart valve implant 16 into a radially expanded and larger profile "deployed" configuration suitable for implantation within the anatomy at the area of interest or the target location. When the replacement heart valve implant 16 is suitably deployed within the anatomy, the outer sheath 12 and/or the medical device system 10 can be removed from the vasculature, leaving the replacement heart valve implant 16 in place in a "released" configuration to function as, for example, a suitable replacement for the native heart valve. In at least some interventions, the replacement heart valve implant 16 may be deployed within the native heart valve (e.g., the native heart valve is left in place and not excised). Alternatively, the native heart valve may be removed and the replacement heart valve implant 16 may be deployed in its place as a replacement.

Disposed within a first lumen of the inner sheath or catheter 14 may be the actuator element, which may be used to actuate and/or translate (e.g., expand and/or elongate) the replacement heart valve implant 16 between the "delivery" configuration and the "deployed" configuration. In some embodiments, the actuator element may include or comprise a plurality of actuator elements, two actuator elements, three actuator elements, four actuator elements, or another suitable or desired number of actuator elements. In some embodiments, each actuator element may be disposed within a separate lumen of the inner sheath or catheter 14.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element" may be equally referred to all instances and quantities beyond one of "the at least one actuator element" or "the plurality of actuator elements".

Figure 2:
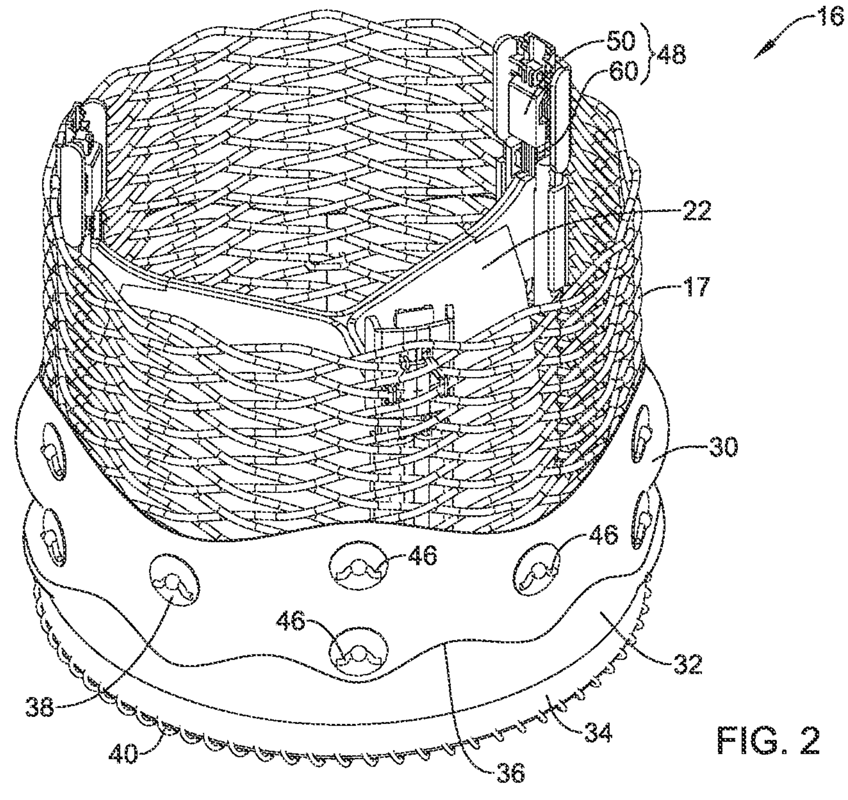
FIG. 2 illustrates an example replacement heart valve implant.

FIG. 2 illustrates some selected components of the medical device system 10 and/or the replacement heart valve implant 16, shown in the "deployed" configuration. The replacement heart valve implant 16 may include an expandable anchor member 17 that is reversibly actuatable between an elongated and/or radially-collapsed "delivery" configuration and an axially-shortened and/or radially-expanded "deployed" configuration. In some embodiments, the expandable anchor member 17 may be tubular and defines a lumen extending coaxially along a central longitudinal axis from a distal or inflow end of the expandable anchor member 17 and/or the replacement heart valve implant 16 to a proximal or outflow end of the expandable anchor member 17 and/or the replacement heart valve implant 16.

In some embodiments, the expandable anchor member 17 may comprise an expandable support structure and/or stent framework, which terms may be used interchangeably with "anchor member" herein. In some embodiments, the support structure and/or the expandable anchor member 17 may comprise a plurality of interconnected struts. In some embodiments, the support structure and/or the expandable anchor member 17 may comprise a self-expanding braided and/or woven mesh structure made up of one or more filaments disposed and/or interwoven circumferentially about the lumen of the support structure and/or the expandable anchor member 17 and/or the replacement heart valve implant 16. Non-self-expanding, mechanically-expandable, and/or assisted self-expanding expandable anchor members are also contemplated. In at least some embodiments, the support structure and/or the expandable anchor member 17 may be formed as a unitary structure (e.g., formed from a single filament or strand of wire, cut from a single tubular member, etc.). In some embodiments, the support structure and/or the expandable anchor member 17 may define a generally cylindrical outer surface in the deployed configuration. An overall length of the support structure and/or the expandable anchor member 17 in the axially-shortened and/or radially-expanded "deployed" configuration may be less than in the elongated and/or radially-collapsed "delivery" configuration. Other configurations are also possible—a cross-section defining a generally elliptical outer surface, for example. Some examples of suitable but non-limiting materials for the replacement heart valve implant 16, the support structure, and/or the expandable anchor member 17, and/or components or elements thereof, are described below.

Also shown in FIG. 2, but omitted from several other figures in the interest of clarity, the replacement heart valve implant 16 may include a plurality of valve leaflets 22 disposed within the lumen of the replacement heart valve implant 16, the support structure, and/or the expandable anchor member 17. In some embodiments, the plurality of valve leaflets 22 may be attached and/or secured to the support structure and/or the expandable anchor member 17 at a plurality of locations within the lumen of the replacement heart valve implant 16, the support structure, and/or the expandable anchor member 17. In some embodiments, the plurality of valve leaflets 22 may be attached and/or secured to the support structure and/or the expandable anchor member 17 using sutures, adhesives, or other suitable means.

In some embodiments, the plurality of valve leaflets 22 may include or comprise two leaflets, three leaflets, four leaflets, etc. as desired. For example, the plurality of valve leaflets 22 may comprise a first valve leaflet, a second valve leaflet, a third valve leaflet, etc., and may be referred to collectively as the plurality of valve leaflets 22. The plurality of valve leaflets 22 of the replacement heart valve implant 16 may be configured to move between an open configuration permitting antegrade fluid flow through the replacement heart valve implant 16 and/or the lumen of the replacement heart valve implant 16, the support structure, and/or the expandable anchor member 17, and a closed configuration preventing retrograde fluid flow through the replacement heart valve implant 16 and/or the lumen of the replacement heart valve implant 16, the support structure, and/or the expandable anchor member 17. The plurality of valve leaflets 22 may each have a free edge, wherein the free edges of the plurality of valve leaflets 22 coapt within the replacement heart valve implant 16, the support structure and/or the expandable anchor member 17, and/or the lumen extending through the replacement heart valve implant 16, the support structure, and/or the expandable anchor member 17 in the closed configuration. Some examples of suitable but non-limiting materials for the plurality of valve leaflets 22 (e.g., the first valve leaflet, the second valve leaflet, the third valve leaflet, etc.) may include bovine pericardial, polymeric materials, or other suitably flexible biocompatible materials.

The replacement heart valve implant 16 may include a replacement heart valve commissure assembly disposed within the lumen of the replacement heart valve implant 16, the support structure, and/or the expandable anchor member 17. In some embodiments, the replacement heart valve implant 16 may include more than one replacement heart valve commissure assembly. For example, each adjacent pair of valve leaflets 22 may form and/or define one replacement heart valve commissure assembly. Therefore, the number of replacement heart valve commissure assemblies may be directly related to the number of valve leaflets 22 (e.g., three valve leaflets form and/or define three replacement heart valve commissure assemblies, two valve leaflets form and/or define two replacement heart valve commissure assemblies, etc.).

In some embodiments, the replacement heart valve implant 16 and/or the replacement heart valve commissure assembly may include a locking mechanism 48 configured to lock the support structure and/or the expandable anchor member 17 in the "deployed" configuration. In some embodiments, the replacement heart valve implant 16 may include or comprise a plurality of locking mechanisms 48, two locking mechanisms 48, three locking mechanisms 48, etc. In some embodiments, each replacement heart valve commissure assembly may correspond to and/or include one corresponding locking mechanism 48. Each locking mechanism 48 may include a first locking portion or a post member 60 secured to the support structure and/or the expandable anchor member 17 and configured to engage with a second locking portion or a buckle member 50 secured to the support structure and/or the expandable anchor member 17.

In some embodiments, the actuator element may be configured to releasably engage the locking mechanism 48 and/or reversibly actuate the support structure and/or the expandable anchor member 17 and/or the replacement heart valve implant 16, the support structure, and/or the expandable anchor member 17 between the "delivery" configuration and the "deployed" configuration and/or the "released" configuration while the actuator element is engaged with the locking mechanism 48. In some embodiments, one actuator element may correspond to, engage with, and/or actuate one locking mechanism 48. In some embodiments, one actuator element may correspond to, engage with, and/or actuate more than one locking mechanism 48. Other configurations are also contemplated.

In some embodiments, the actuator element may include a proximal end and a distal end. In use, the proximal end may be operatively connected to the handle 18, and/or manipulated or otherwise actuated by a user using the handle 18, to reversibly shift the replacement heart valve implant 16 between the "delivery" configuration and the "deployed" configuration. In some embodiments, the actuator element may be axially translatable relative to the first locking portion or post member 60 and/or the second locking portion or buckle member 50 of the replacement heart valve implant 16. In some embodiments, the actuator element may be releasably coupled to the first locking portion or post member 60. The handle 18 may be configured to actuate and/or translate the actuator element (e.g., each actuator element, etc.) relative to the outer sheath 12, the replacement heart valve implant 16, the corresponding locking mechanism(s) 48 (e.g., the plurality of locking mechanisms 48, etc.), and/or the first locking portion or post member 60 in the "delivery" and/or "deployed" configuration.

In some embodiments, the actuator element may be generally round, oblong, ovoid, rectangular, polygonal (i.e., two-sided, three-sided, four-sided, five-sided, six-sided, etc.) and/or combinations thereof in shape. Other shapes, both regular and irregular, are also contemplated. In some embodiments, the actuator element may be formed from a single piece of wire, round stock, or other suitable material. In some embodiments, the actuator element may be formed by further processing the single piece of wire, round stock, or other suitable material, such as by machining, stamping, laser cutting, etc. Some suitable but non-limiting materials for the actuator element, for example metallic materials or polymeric materials, are described below.

In some embodiments, the replacement heart valve implant 16 may include a seal member 30 comprising a tubular polymeric seal element configured to be circumferentially disposed on and/or around at least a portion of an outer surface of the replacement heart valve implant 16, the support structure, and/or the expandable anchor member 17. The tubular polymeric seal element may define a central longitudinal axis of the seal member 30, the replacement heart valve implant 16, the support structure, and/or the expandable anchor member 17. In some embodiments, the seal member 30 and/or the tubular polymeric seal element may be fixedly attached and/or secured to the distal or inflow end of the replacement heart valve implant 16, the support structure and/or the expandable anchor member 17, and/or the seal member 30 and/or the tubular polymeric seal element may be fixedly attached and/or secured to the plurality of valve leaflets 22 proximate the distal or inflow end of the replacement heart valve implant 16, the support structure, and/or the expandable anchor member 17. The seal member 30 and/or the tubular polymeric seal element may be sufficiently flexible and/or pliable to engage, conform to, and/or seal against native valve leaflets and/or a native heart valve annulus in the axially-shortened and/or radially-expanded "deployed" configuration, thereby sealing an exterior of the replacement heart valve implant 16, the support structure, and/or the expandable anchor member 17 within and/or against the native heart valve annulus and/or the native valve leaflets and preventing leakage around the replacement heart valve implant 16, the support structure, and/or the expandable anchor member 17.

In some embodiments, the seal member 30 and/or the tubular polymeric seal element may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other suitable polymeric materials are also contemplated, some of which are discussed below.

In some embodiments, the seal member 30 and/or the tubular polymeric seal element may include a reinforcement strip 32 fixedly attached to the seal member 30 and/or the tubular polymeric seal element proximate a first end of the tubular polymeric seal element, for example, at and/or adjacent the distal end and/or the inflow end of the support structure and/or the expandable anchor member 17, the seal member 30, and/or the tubular polymeric seal element. In at least some embodiments, the reinforcement strip 32 may extend circumferentially around the central longitudinal axis of the seal member 30, the replacement heart valve implant 16, the support structure, and/or the expandable anchor member 17. In some embodiments, the reinforcement strip 32 may include a scalloped downstream edge 36 to reduce bunching and/or bulk when in the delivery configuration.

In some embodiments, the reinforcement strip 32 may be integrally formed with, incorporated into, adhered to, and/or at least partially embedded within the seal member 30 and/or the tubular polymeric seal element. In some embodiments, the reinforcement strip 32 may be formed from a woven or nonwoven fabric strip, a textile, or other thin flexible material. The reinforcement strip 32 may include a radiopaque element 34 extending circumferentially around the central longitudinal axis of the seal member 30, the replacement heart valve implant 16, the support structure, and/or the expandable anchor member 17. In some embodiments, the radiopaque element 34 may be at least partially embedded in the reinforcement strip 32. In some embodiments, the radiopaque element 34 may extend completely around the central longitudinal axis of the seal member 30, the replacement heart valve implant 16, the support structure, and/or the expandable anchor member 17. In at least some embodiments, the radiopaque element 34 may be disposed at and/or adjacent the distal end and/or the inflow end of the support structure and/or the expandable anchor member 17, the seal member 30, and/or the tubular polymeric seal element. In some embodiments, the radiopaque element 34 may be disposed at a distalmost portion of the support structure and/or the expandable anchor member 17, the seal member 30, the tubular polymeric seal element, and/or the reinforcement strip 32.

In some embodiments, the radiopaque element 34 may include a polyurethane spray coating doped with radiopaque nanoparticles. In some embodiments, the polyurethane spray coating may be disposed on the reinforcement strip 32. In some embodiments, the polyurethane spray coating may be intermingled with the reinforcement strip 32 (e.g., as a matrix having and/or supporting a fiber reinforcement therein, etc.). In some embodiments, the radiopaque nanoparticles may include one or more of the following: tungsten, platinum, tantalum, cobalt, chromium, nickel, titanium, gold, and palladium. Other suitable radiopaque, biocompatible materials are also contemplated. In some embodiments, the reinforcement strip 32 and/or the radiopaque element 34 may be formed from an electrospun polyester matrix doped with radiopaque nanoparticles. In some embodiments, the reinforcement strip 32 and/or the radiopaque element 34 may be formed from a chopped radiopaque fiber-polyester matrix.

The reinforcement strip 32 may provide tear resistance in the vicinity of sutures, filaments, or other attachment elements associated with components or aspects of the replacement heart valve implant 16. In some embodiments, the seal member 30 and/or the reinforcement strip 32 may extend longitudinally beyond the distal end and/or the inflow end of the support structure and/or the expandable anchor member 17.

In some embodiments, a distal end of each one of the plurality of valve leaflets 22 may be secured directly to the reinforcement strip 32 and/or a distal end of the reinforcement strip 32. In some embodiments, the plurality of valve leaflets 22 may not be secured directly to the distal end of the support structure and/or the expandable anchor member 17. In some embodiments, the reinforcement strip 32 may include a plurality of perforations extending through the reinforcement strip 32 and/or the seal member 30. In some embodiments, the plurality of perforations may accommodate sutures passing therethrough (e.g., through the reinforcement strip 32 and/or the seal member 30) to secure elements or aspects of the replacement heart valve implant 16, such as (but not limited to) the plurality of valve leaflets 22, the support structure, and/or the expandable anchor member 17, for example.

In some embodiments, one or more whip sutures 40 may attach a distal end of the seal member 30 to a distal end of the plurality of valve leaflets 22 adjacent and/or at the distal or inflow end of the support structure and/or the expandable anchor member 17. In some embodiments, the one or more whip sutures 40 may attach the reinforcement strip 32 and/or a distal end of the reinforcement strip 32 to the distal end of the plurality of valve leaflets 22 adjacent and/or at a distal or inflow end of the support structure and/or the expandable anchor member 17. In some embodiments, the one or more whip sutures 40 may form one or more first helical spirals oriented in a first direction. In some embodiments, the one or more whip sutures 40 may include and/or form a plurality of windings.

In some embodiments, a plurality of proximal lashing sutures 46 may attach a proximal portion of the seal member 30 to a central portion and/or a distal portion of the support structure and/or the expandable anchor member 17. In some embodiments, at least one grommet 38 may be disposed along an outer surface of the seal member 30 and/or at least partially embedded within the seal member 30 at each of the plurality of proximal lashing sutures 46 to aid in attaching the seal member 30 to the support structure and/or the expandable anchor member 17. In some embodiments, the plurality of proximal lashing sutures 46 may extend through the at least one grommet 38. In some embodiments, the plurality of proximal lashing sutures 46 may attach the proximal portion of the seal member 30 to the central portion and/or the distal portion of the support structure and/or the expandable anchor member 17 proximal of the distal or inflow end of the support structure and/or the expandable anchor member 17.

During delivery, the replacement heart valve implant 16, the support structure, and/or the expandable anchor member 17 may be secured at the distal end of the inner sheath or catheter 14 by a plurality of fingers of a coupler coupled to a projecting portion at a proximal end of the second locking portion or buckle member 50 and/or a plurality of release pins securing together the actuator element and the first locking portion or post member 60. The plurality of release pins may releasably secure the actuator element to the first locking portion or post member 60, thereby limiting relative axial movement between the actuator element and the first locking portion or post member 60 and forms a configuration of these structures that can be utilized during delivery of the replacement heart valve implant 16.

After the replacement heart valve implant 16, the support structure, and/or the expandable anchor member 17 is advanced within the anatomy and/or vasculature to the area of interest, the actuator element can be used to actuate the replacement heart valve implant 16, the support structure, and/or the expandable anchor member 17 to the "deployed" configuration by proximally retracting the actuator element relative to the second locking portion or buckle member 50, the support structure, and/or the expandable anchor member 17, thereby pulling the first locking portion or post member 60 into engagement with the second locking portion or buckle member 50. Finally, the plurality of release pins can be removed using the handle 18, thereby uncoupling the actuator element from the first locking portion or post member 60, which allows the replacement heart valve implant 16 to be released from the medical device system 10 in the "released" configuration.

In some embodiments, the first locking portion or post member 60 and the second locking portion or buckle member 50 may be longitudinally movable relative to each other along an inner surface of the support structure and/or the expandable anchor member 17 in the "delivery" configuration and/or the "deployed" configuration. In some embodiments, the first locking portion or post member 60 may be non-releasably secured to a distal portion and/or proximate the distal or upstream end of the support structure and/or the expandable anchor member 17 along the inner surface of the support structure and/or the expandable anchor member 17. In some embodiments, the second locking portion or buckle member 50 may be fixedly secured to a proximal portion and/or proximate the proximal or downstream end of the support structure and/or the expandable anchor member 17 against the inner surface of the expandable anchor member 17. The second locking portion or buckle member 50 may be configured to slidably receive at least a portion of the first locking portion or post member 60 therein.

In some embodiments, the first locking portion or post member 60 may be disposed within the lumen of the replacement heart valve implant 16, the support structure, and/or the expandable anchor member 17 proximate the distal or inflow end of the replacement heart valve implant 16, the support structure, and/or the expandable anchor member 17 when the support structure and/or the expandable anchor member 17 is in the elongated "delivery" configuration and/or the "everted" configuration. In some embodiments, at least a portion of the first locking portion or post member 60 may be disposed distal of the support structure and/or the expandable anchor member 17 when the support structure and/or the expandable anchor member 17 is in the elongated "delivery" configuration and/or the "everted" configuration. In some embodiments, the first locking portion or post member 60 may be configured to engage the second locking portion or buckle member 50 to lock the replacement heart valve implant 16, the support structure, and/or the expandable anchor member 17 in the "deployed" configuration. Some suitable but non-limiting materials for the first locking portion or post member 60, for example metallic materials or polymeric materials, are described below.

The second locking portion or buckle member 50 may include a base portion, a body portion defining a longitudinal channel extending through the body portion, and a flap portion extending proximally and/or toward the proximal end of the base portion from the body portion of the second locking portion or buckle member 50. In at least some embodiments, the flap portion of the second locking portion or buckle member 50 may be configured to engage the first locking portion or post member 60 to lock the replacement heart valve implant 16, the support structure, and/or the expandable anchor member 17 in the "deployed" configuration. Some suitable but non-limiting materials for the second locking portion or buckle member 50, for example metallic materials or polymeric materials, are described below.

After the replacement heart valve implant 16 is advanced within the anatomy and/or the vasculature to the area of interest, the outer sheath 12 may be translated and/or actuated proximally to expose the replacement heart valve implant 16. Then, the actuator element can be actuated (e.g., proximally retracted) to axially shorten and/or radially expand the replacement heart valve implant 16, the support structure, and/or the expandable anchor member 17 from the "delivery" configuration toward the "deployed" configuration by proximally retracting and/or translating the actuator element to pull the first locking portion or post member 60 into engagement with the second locking portion or buckle member 50, using the handle 18 for example. After verifying satisfactory placement of the replacement heart valve implant 16, such as by an appropriate imaging technique, the actuator element may each be decoupled from the first locking portion or post member 60, which allows the distal portion of the actuator element to be pulled proximally out of the second locking portion or buckle member 50, thereby leaving the replacement heart valve implant 16, the support structure, and/or the expandable anchor member 17 at the area of interest in a "released" configuration.

Figure 3:
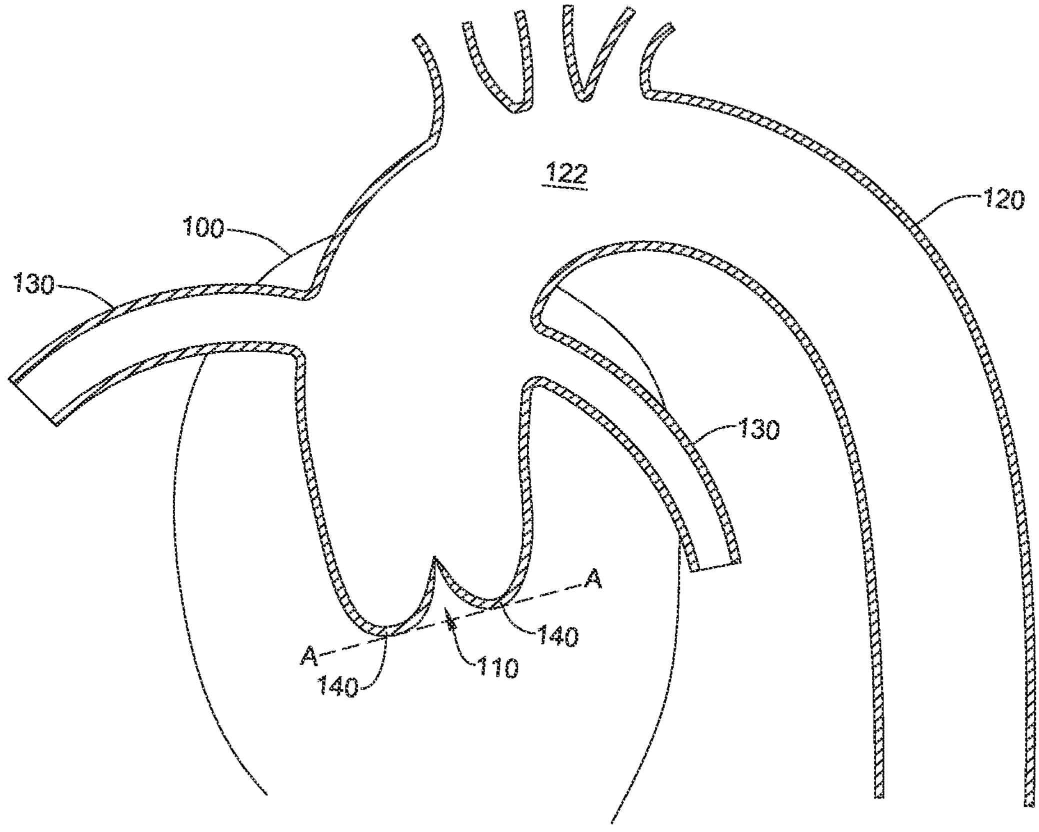
FIG. 3 a schematic view of a portion of a heart and certain connected vasculature.

FIG. 3 illustrates a schematic view of a portion of a patient's heart 100 and certain connected vasculature, such as the aorta 120 connected to the heart 100 by the aortic arch 122, and the coronary arteries 130. Native valve leaflets 140 of a native heart valve 110 (e.g., an aortic valve, a mitral valve, etc.) may be seen schematically where the aorta 120 (disposed downstream of the native valve leaflets 140) meets and/or joins the heart 100 and in fluid communication with a left ventricle of the heart 100 (disposed upstream of the native valve leaflets 140). On a downstream side of the native valve leaflets 140 is an area described herein as a cusp, where the cusp is a space between the native valve leaflets 140 and a wall of the aorta 120 and/or the aortic arch 122 immediately downstream of and/or adjacent to the native heart valve 110 (e.g., the aortic valve, etc.). The native valve leaflets 140 meet or intersect at a commissure configured to reversibly and/or selectively permit antegrade fluid flow and prevent retrograde fluid flow through the native heart valve 110. As such, a tricuspid heart valve, such as a normal aortic valve, will include and/or define three commissures and three cusps. Similarly, a bicuspid heart valve will include and/or define two commissures and two cusps. For the purpose of understanding the placement of the replacement heart valve implant 16, a reference plane A-A may be identified extending through an annulus of the native heart valve 110 generally perpendicular to a direction of fluid flow through the native heart valve 110, as shown in FIG. 3.

A method of locating a replacement heart valve implant 16 during an implantation procedure may comprise advancing the replacement heart valve implant 16 through a vasculature (e.g., the aorta 120, the aortic arch 122, etc.) toward a native heart valve 110 (e.g., the aortic valve, etc.) in an elongated and/or radially-collapsed "delivery" configuration within the outer sheath 12. The replacement heart valve implant 16 may be constructed and/or arranged as described herein. In some embodiments, the medical device system 10, the outer sheath 12, and/or the replacement heart valve implant 16 may be advanced through the vasculature (e.g., the aorta 120, the aortic arch 122, etc.) within an optional introducer sheath 200, as illustrated in FIG. 4 for example.

Figure 4:
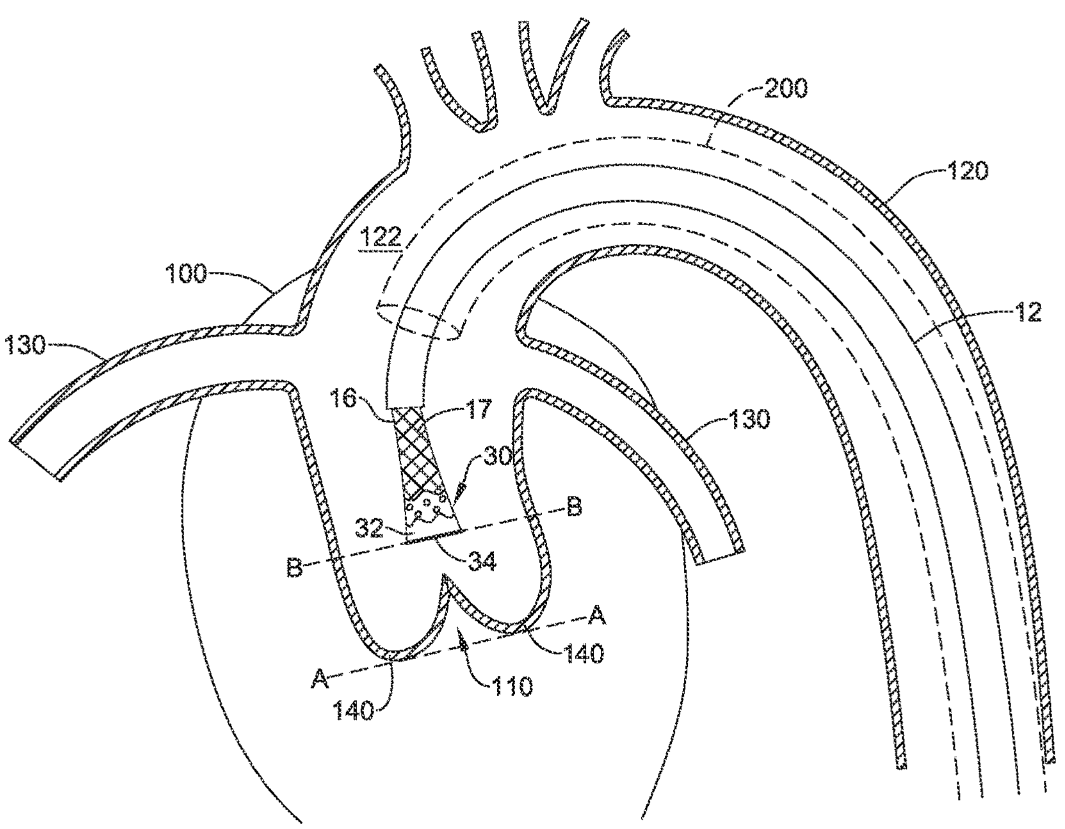
FIG. 4-6 illustrate aspects of deploying a replacement heart valve implant.
Figure 5:
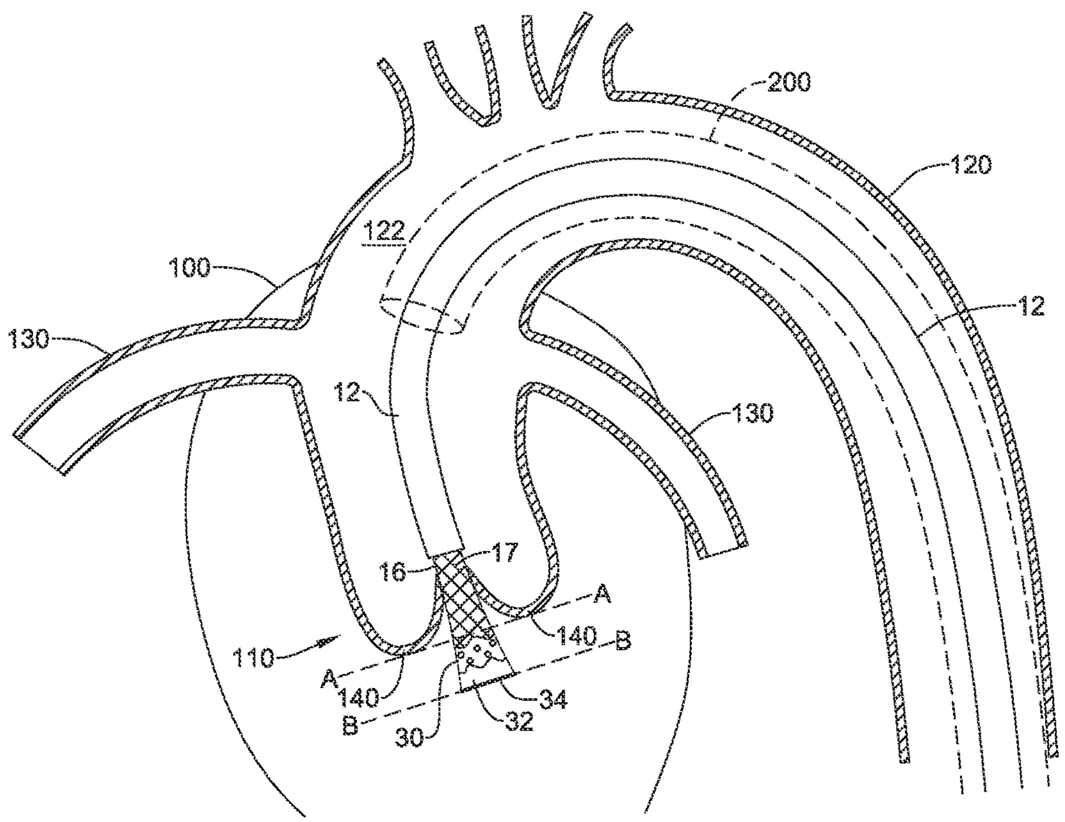
Figure 6:
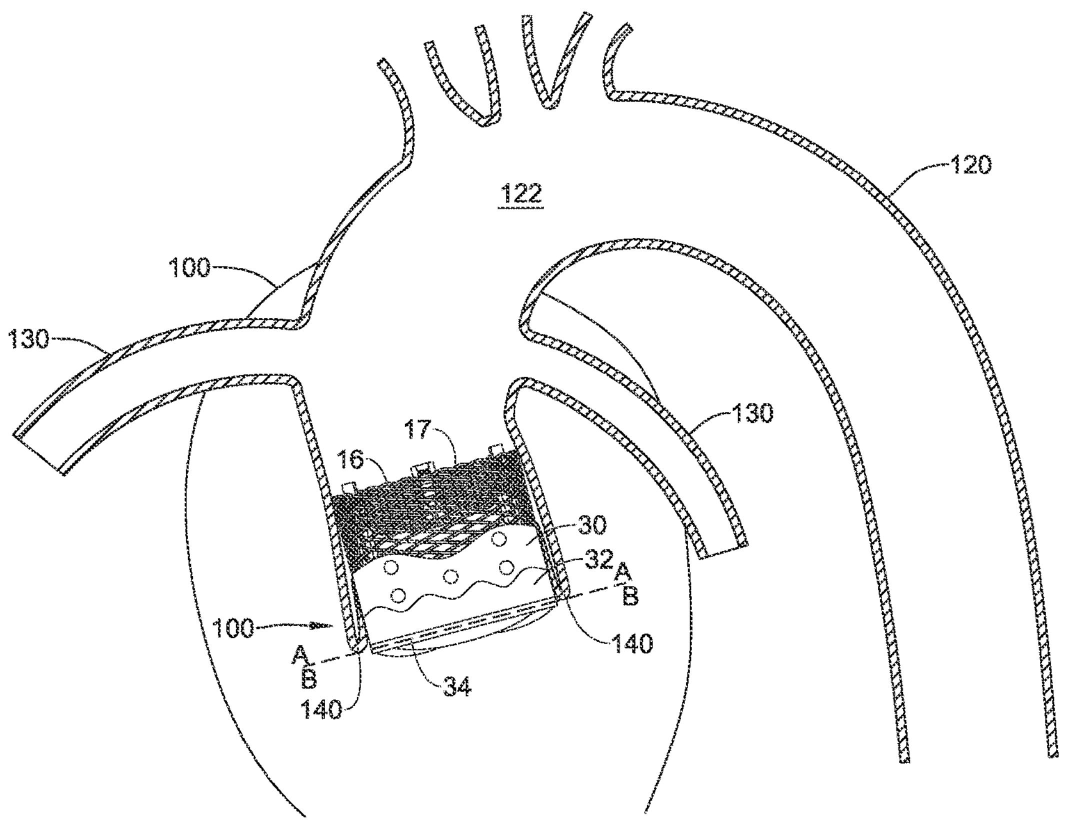

The replacement heart valve implant 16 may be exposed and/or deployed from the outer sheath 12 at and/or adjacent to the native heart valve 110, as seen in FIGS. 4-6. In some embodiments, the replacement heart valve implant 16 may be exposed and/or deployed from the outer sheath 12 just downstream of the native heart valve 110 (e.g., FIG. 4), just upstream of the native heart valve 110 (e.g., FIG. 5), within the native heart valve 110 (e.g., FIG. 6), and/or combinations thereof. As described herein, the reinforcement strip 32 may include a radiopaque element 34 extending circumferentially around the central longitudinal axis of the seal member 30, the replacement heart valve implant 16, the support structure, and/or the expandable anchor member 17 in a first plane B-B, shown in FIG. 4. The first plane B-B may be used to locate and/or position the replacement heart valve implant 16 relative to the annulus of the native heart valve 110.

For example, the method may include imaging the replacement heart valve implant 16, the support structure, and/or the expandable anchor member 17 within the vasculature (e.g., the aorta 120, the aortic arch 122, etc.) and the native heart valve 110 concurrently as the replacement heart valve implant 16 approaches and/or is disposed within the native heart valve 110, using a suitable imaging technique (e.g., X-ray, fluoroscopy, etc.). The imaging may identify the reference plane A-A extending through the annulus of the native heart valve 110 generally perpendicular to the direction of fluid flow through the native heart valve 110. In some embodiments, an offset of the first plane B-B from the reference plane A-A may be measured to aid in locating and/or placing the replacement heart valve implant 16, the support structure, and/or the expandable anchor member 17 relative to the annulus of the native heart valve 110, as seen in FIGS. 4 and 5. For example, reduced and/or limited intrusion of the replacement heart valve implant 16 into the left ventricle of the heart 100 may be desirable in some procedures and/or patients.

In some embodiments, the method may include, after initial imaging and/or during imaging, moving the replacement heart valve implant 16, the support structure, and/or the expandable anchor member 17 to translate the first plane B-B upstream toward the reference plane A-A if the first plane B-B is initially offset too far downstream. In some embodiments, the method may include, after initial imaging and/or during imaging, moving the replacement heart valve implant 16, the support structure, and/or the expandable anchor member 17 to translate the first plane B-B downstream toward the reference plane A-A if the first plane B-B is initially offset too far upstream.

The method may further include expanding the replacement heart valve implant 16, the support structure, and/or the expandable anchor member 17 within the native heart valve 110 with the first plane B-B positioned substantially parallel to the reference plane A-A and offset axially and/or in the direction of fluid flow less than 4 mm (millimeters) from the reference plane A-A. In some embodiments, the first plane B-B may be positioned substantially parallel to the reference plane A-A and offset axially and/or in the direction of fluid flow less than 2 mm (millimeters) from the reference plane A-A. In some embodiments, the first plane B-B may be positioned substantially coplanar with the reference plane A-A, as shown in FIG. 6 for example.

In some embodiments, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. and/or components thereof (such as, but not limited to, the actuator element, the support structure and/or expandable anchor member 17, the at least one grommet 38, the whip sutures 40, the proximal lashing sutures 46, the second locking portion or buckle member 50, the first locking portion or post member 60, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like);

platinum enriched stainless steel; titanium; platinum; palladium; gold; combinations thereof; and the like; or any other suitable material.

As alluded to herein, within the family of commercially available nickel-titanium or nitinol alloys, is a category designated “linear elastic” or “non-super-elastic” which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial “superelastic plateau” or “flag region” in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed “substantially” linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 10, the outer sheath 12, the inner sheath or catheter 14, the replacement heart valve implant 16, the handle 18, the seal member 30, the reinforcement strip 32, the radiopaque element 34, the introducer sheath 200, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. to achieve the same result.

In some embodiments, a degree of Magnetic Resonance Imaging (MM) compatibility is imparted into the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. For example, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc., and/or components or portions thereof, may be made of a material that does not substantially distort the image and create substantial artifacts (e.g., gaps in the image). Certain ferromagnetic materials, for example, may not be suitable because they may create artifacts in an Mill image. The medical device system 10, the outer sheath 12, the inner sheath or catheter 14, the replacement heart valve implant 16, the handle 18, the seal member 30, the reinforcement strip 32, the radiopaque element 34, the introducer sheath 200, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 10, the outer sheath 12, the inner sheath or catheter 14, the replacement heart valve implant 16, the handle 18, the seal member 30, the reinforcement strip 32, the radiopaque element 34, the introducer sheath 200, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasco-active mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of locating a replacement heart valve implant during an implantation procedure, comprising:

advancing the replacement heart valve implant within an outer sheath through a vasculature toward a native heart valve in a collapsed delivery configuration, the replacement heart valve implant comprising an expandable tubular support structure defining a central longitudinal axis, a plurality of valve leaflets disposed within the tubular support structure, and a radiopaque element extending circumferentially around the central longitudinal axis in a first plane adjacent an inflow end region of the tubular support structure;

imaging the replacement heart valve implant within the vasculature and the native heart valve concurrently as the replacement heart valve implant approaches the native heart valve, wherein the imaging identifies a reference plane extending through an annulus of the native heart valve generally perpendicular to a direction of fluid flow through the native heart valve; and expanding the tubular support structure into a deployed configuration within the native heart valve with the first plane positioned substantially parallel to the reference plane and offset less than 4 mm from the reference plane.

2. The method of claim 1, wherein the first plane is offset less than 2 mm from the reference plane.

3. The method of claim 1, wherein the first plane is positioned substantially coplanar with the reference plane.

4. The method of claim 1, further comprising a reinforcement strip coupled to the tubular support structure adjacent the inflow end region.

5. The method of claim 4, wherein the radiopaque element includes radiopaque nanoparticles embedded in the reinforcement strip.

6. The method of claim 5, wherein the replacement heart valve implant includes a seal member disposed on an outer surface of the tubular support structure, and the reinforcement strip is attached to the seal member.

7. The method of claim 6, wherein the radiopaque element is disposed at a distalmost portion of the seal member.

8. The method of claim 4, wherein the reinforcement strip includes a scalloped downstream edge.

9. The method of claim 1, wherein if, during and/or after imaging, the first plane is positioned more than 4 mm downstream of the native heart valve, then the method further includes moving the replacement heart valve implant to translate the first plane upstream toward the reference plane.

10. The method of claim 1, wherein if, during and/or after imaging, the first plane is positioned more than 4 mm upstream of the native heart valve, then the method further includes moving the replacement heart valve implant to translate the first plane downstream toward the reference plane.

11. The method of claim 1, wherein the replacement heart valve implant includes one or more locking mechanism configured to lock the expandable tubular support structure in the deployed configuration, wherein after expanding the tubular support structure into the deployed configuration within the native heart valve, the method further comprises actuating the one or more locking mechanism to lock the expandable tubular support structure in the deployed configuration.

12. The method of claim 11, wherein each locking mechanism includes a first locking portion and a second locking portion.

13. A method of locating a replacement heart valve implant during an implantation procedure, comprising:

advancing the replacement heart valve implant within an outer sheath through a vasculature toward a native heart valve in a collapsed delivery configuration, the replacement heart valve implant comprising an expandable tubular support structure defining a central longitudinal axis, a plurality of valve leaflets disposed within the tubular support structure, a seal member disposed on an outer surface of the tubular support structure, a reinforcement strip coupled to the seal member, and a radiopaque element extending circumferentially around the central longitudinal axis in a first plane adjacent an inflow end region of the tubular support structure;

imaging the replacement heart valve implant within the vasculature and the native heart valve concurrently as the replacement heart valve implant approaches the native heart valve, wherein the imaging identifies a reference plane extending through an annulus of the native heart valve generally perpendicular to a direction of fluid flow through the native heart valve; and expanding the tubular support structure into a deployed configuration within the native heart valve with the first plane positioned substantially parallel to the reference plane and offset less than 4 mm from the reference plane.

14. The method of claim 13, wherein the first plane is offset less than 2 mm from the reference plane.

15. The method of claim 13, wherein the first plane is positioned substantially coplanar with the reference plane.

16. The method of claim 13, wherein the radiopaque element includes radiopaque nanoparticles embedded in the reinforcement strip.

17. The method of claim 13, wherein the radiopaque element extends completely around the central longitudinal axis.

18. The method of claim 13, wherein if, during and/or after imaging, the first plane is positioned more than 4 mm downstream of the native heart valve, then the method further includes moving the replacement heart valve implant to translate the first plane upstream toward the reference plane.

19. The method of claim 13, wherein if, during and/or after imaging, the first plane is positioned more than 4 mm upstream of the native heart valve, then the method further includes moving the replacement heart valve implant to translate the first plane downstream toward the reference plane.

20. A method of locating a replacement heart valve implant during an implantation procedure, comprising:

advancing the replacement heart valve implant within an outer sheath through a vasculature toward a native heart valve in a collapsed delivery configuration, the replacement heart valve implant comprising an expandable tubular support structure defining a central longitudinal axis, a plurality of valve leaflets disposed within the tubular support structure, and a radiopaque element extending circumferentially around the central longitudinal axis in a first plane adjacent an inflow end region of the tubular support structure;

imaging the replacement heart valve implant within the vasculature and the native heart valve concurrently as the replacement heart valve implant approaches the native heart valve, wherein the imaging identifies a reference plane extending through an annulus of the native heart valve generally perpendicular to a direction of fluid flow through the native heart valve; and expanding the tubular support structure into a deployed configuration within the native heart valve with the first plane positioned substantially parallel to the reference plane and offset less than 4 mm from the reference plane;

wherein if, during and/or after imaging, the first plane is positioned more than 4 mm downstream of the native heart valve, then the method further includes moving the replacement heart valve implant to translate the first plane upstream toward the reference plane, and wherein if, during and/or after imaging, the first plane is positioned more than 4 mm upstream of the native heart valve, then the method further includes moving the replacement heart valve implant to translate the first plane downstream toward the reference plane.

* * * * *